United States Patent
Mandel et al.

(10) Patent No.: US 11,813,330 B2
(45) Date of Patent: Nov. 14, 2023

(54) SONODYNAMIC THERAPY USING SONODYNAMICALLY ACTIVATED COORDINATION COMPLEXES OF TRANSITION METALS AS SENSITIZING AGENTS

(71) Applicant: Theralase Technologies, Inc., Toronto (CA)

(72) Inventors: Arkady Mandel, North York (CA); Roger Dumoulin-White, Toronto (CA)

(73) Assignee: THERALASE TECHNOLOGIES, INC., Toronto (CA)

( * ) Notice: Subject to any disclaimer, the term of this patent is extended or adjusted under 35 U.S.C. 154(b) by 239 days.

(21) Appl. No.: 17/192,569

(22) Filed: Mar. 4, 2021

(65) Prior Publication Data
US 2022/0296709 A1  Sep. 22, 2022

(51) Int. Cl.
| A61K 41/00 | (2020.01) |
| A61N 7/00 | (2006.01) |
| A61N 5/06 | (2006.01) |
| A61K 31/33 | (2006.01) |
| A61K 38/40 | (2006.01) |
| A61N 5/067 | (2006.01) |
| A61K 47/64 | (2017.01) |
| A61P 35/00 | (2006.01) |

(52) U.S. Cl.
CPC .......... *A61K 41/0033* (2013.01); *A61K 31/33* (2013.01); *A61K 38/40* (2013.01); *A61N 5/06* (2013.01); *A61N 7/00* (2013.01); *A61P 35/00* (2018.01); *A61N 5/067* (2021.08); *A61N 2007/0004* (2013.01)

(58) Field of Classification Search
CPC ................ A61K 41/0033; A61K 38/40; A61K 41/0057; A61K 47/644; A61N 5/06; A61N 7/00; A61N 5/067; A61N 2007/0004; A61N 5/062; A61P 35/00
See application file for complete search history.

(56) References Cited

U.S. PATENT DOCUMENTS

| 5,632,970 | A | 5/1997 | Sessler et al. |
| 6,498,945 | B1 | 12/2002 | Alfheim et al. |
| 8,318,794 | B2 | 11/2012 | Wang et al. |
| 8,758,725 | B2 | 6/2014 | Sharma et al. |
| 9,220,718 | B2 | 12/2015 | Park et al. |
| 2003/0082101 | A1 | 5/2003 | Taylor et al. |
| 2010/0262115 | A1 | 10/2010 | Madiyalakan et al. |
| 2015/0374216 | A1 | 12/2015 | Chae |
| 2016/0039854 | A1* | 2/2016 | McFarland ......... C07F 15/0026 546/10 |
| 2017/0304648 | A1 | 10/2017 | Mandel et al. |

FOREIGN PATENT DOCUMENTS

| CN | 102670512 A | 9/2012 |
| WO | 9852610 A1 | 11/1998 |
| WO | 2012143739 A1 | 10/2012 |

OTHER PUBLICATIONS

English Abstract for CN 102670512 A (2012).
Chen et al. (2012). Use of a novel sonosensitizer in sonodynamic therapy of U251 glioma cells in vitro. Experimental and Therapeutic Medicine, 3, 273-278.
Li et al. (2015). Pulsed high intensity focused ultrasound (pHIFU) enhances delivery of doxorubicin in a preclinical model of pancreatic cancer. Cancer Res., 75(18), 3738-3746.
Monro et al. (2019). Transition metal complexes and photodynamic therapy from a tumor-centered approach: challenges, opportunities, and highlights from the development of TLD1433. Chem Rev., 119(2), 797-828.
Wan et al. (2016). Recent advances of sonodynamic therapy in cancer treatment. Cancer Biol Med, 13(3), 325-338.
Wang et al. (2014). Ultrasound and microbubble guided drug delivery: mechanistic understanding and clinical implications. Curr Pharm Biotechnol, 14(8), 743-752.
Chen et al. (2006). Using Nanoparticles to Enable Simultaneous Radiation and Photodynamic Therapies for Cancer Treatment. Journal of Nanoscience and Nanotechnology, vol. 6, 1159-1166.
Cheng et al. "Bottom Up Synthesis of Metal Ion Doped WS2 Nanoflakes for Cancer Theranostics." ACS Nano. Nov. 24, 2015;9(11):11090 101. doi: 10.1021/acsnano.5b04606. Epub Oct. 9, 2015).

(Continued)

*Primary Examiner* — Joseph R Kosack
*Assistant Examiner* — Sagar Patel
(74) *Attorney, Agent, or Firm* — CAESAR RIVISE, PC

(57) ABSTRACT

A method for destroying cells and/or microorganisms in an organism includes the following steps: (a) administering to the organism a composition including a sonosensitizing compound containing at least one transition metal with three bidentate ligands; and (b) exposing the sonosensitizing compound in the organism to ultrasound, wherein the ultrasound is effective to activate the sonosensitizing compound to destroy at least one of the cells and the microorganisms in the organism. The ultrasound is preferably used in conjunction with electromagnetic therapies comprising photodynamic therapy, low-level laser therapy, and radiation therapy. The ultrasound is preferably administered at a duty cycle in the range from 5% to 95% at a power density of 10 W/cm$^2$ and a frequency in the range from 10 Hz to 10 MHz.

22 Claims, 3 Drawing Sheets

(56) References Cited

OTHER PUBLICATIONS

Deng et al., "Rational Design of Ruthenium Complexes Containing 2,6-Bis(benzimidazolyl)pyridine Derivatives with Radiosensitization Activity by Enhancing p53 Activation. ChemMedChem." Jun. 2015;10(6):991-8. doi: 10.1002/cmdc.201500127. Epub Apr. 27, 2015).

Sazgarnia et al. (2013). In vitro survival of MCF-7 breast cancer cells following combined treatment with ionizing radiation and mitoxantrone-mediated photodynamic therapy. Photodiagnosis and photodynamic therapy, 10(1), 72-78.

\* cited by examiner

SONODYNAMIC THERAPY USING SONODYNAMICALLY ACTIVATED COORDINATION COMPLEXES OF TRANSITION METALS AS SENSITIZING AGENTS

BACKGROUND OF THE INVENTION

1. Field of Invention

This invention relates to sonodynamic therapy and more particularly to Sono Dynamic Therapy ("SDT") using sensitizing agents activated by sonic waves.

2. Description of Related Art

Sonodynamic Therapy

SDT, or therapeutic ultrasound, has been used in various medical applications where activating energy is deposited into tissue to induce biological effects. High-intensity focused ultrasound causes thermal or mechanical changes in specific tissue areas, often used to dissolve obstructions within the body such as blood clots or kidney stones. When combined with imaging modalities such as magnetic resonance imaging ("MRI") or capsule endoscopy, therapeutic ultrasound can be continuously transmitted or administered in pulses to provide targeted ultrasound treatments (US 20150374216A1).

Standard SDT and metronomic SDT (wherein a drug or regimen of drugs is/are administered in low doses at regular intervals over an extended period of time) have been utilized to promote tumor-cell apoptosis by driving the creation of free radicals and cytotoxic Reactive Oxygen Species ("ROS"). See, e.g., US 20030082101A1, US 6498945B1 and W01998052610A1. Sonosensitizers have been used in conjunction with therapeutic ultrasound to enhance the sonic wave effect. As the sonosensitizers remain in oncogenic cells longer than other cells, ROS and free radical generation may be spatially and temporally controlled to target only cancerous tissues based on when the patient is exposed to the sonic waves. Various sonosensitizer formulations have been attempted in the past. U.S. Pat. No. 9,220,718B2 and CN 102670512A disclose sonosensitizers based on liposome complexes and U.S. Pat. No. 8,758,725B2 discloses utilizing perylenequinone derivatives. Additionally, U.S. Pat. No. 8,318,794B2 discloses administering porphyrin-based sonosensitizers to a patient for the purposes of sonodynamic therapy, while US 20030082101 A1 discloses metal-based sonosensitizers. Sonosensitizers can be administered with or without the use of lipid formulations or nanocapsules (WO 2012143739A1 and US 20100262115A1). However, these developments have varied in efficacy in targeting cancerous cells and promoting efficient cellular uptake of sonosensitizing compounds.

Improvements have been made in the field of photodynamic therapy using transition metals to enhance cancer cell apoptosis. See, e.g., U.S. 20170304648. However, the mechanism behind sonodynamic therapy is not completely understood, and the prior art could be improved upon to provide enhanced compositions and methods for conducting SDT.

Use of Transition Metals in Compounds

The use of transition metal-based compounds for photodynamic therapy is increasing (Cheng et al., "Bottom-Up Synthesis of Metal-Ion-Doped WS2 Nanoflakes for Cancer Theranostics." ACS Nano. 2015 November 24;9(11):11090-101. doi: 10.1021/acsnano.5b04606. Epub 2015 Oct. 9). The standard aim for the inclusion of the transition metal is to increase functionality, for example, through their strong near-infrared absorbance and radiation attenuation ability enabling contrasts in photoacoustic imaging and computed tomography. In addition, Gd(III) doping offers the nanostructure a paramagnetic property for MRI; however, transition metal utilization in sonodynamic therapy needs improvement.

Transition Metals: Role of Ligands

In recent years, it has also become more evident that ligands of metal complexes are essential to the efficacy of transition metals in initiating apoptosis in cancer cells (Deng et al., "Rational Design of Ruthenium Complexes Containing 2,6-Bis(benzimidazolyl)pyridine Derivatives with Radiosensitization Activity by Enhancing p53 Activation. ChemMedChem." 2015 June;10(6):991-8. doi: 10.1002/cmdc.201500127. Epub 2015 Apr. 27). The Ru-based complexes in Deng et al. amplified X-ray induced Reactive Oxygen Species ("ROS") generation and consequent DNA damage resulting in cell cycle disruption and induction of apoptosis. The effect in cell growth inhibition was, however, relatively small, not exceeding 2.5-fold for one of the three compounds and less than 2-fold for the other two compounds.

Synergy

Among the advantages of the combined SDT and light, radiation, low level laser, or transferrin therapy is a synergistic effect that is greater than the additive effect.

Safety

Additive effects ensure greater safety of combined treatment by allowing lower doses of irradiation during the treatment (Chen & Zhang, 2006; U.S. Pat. No. 5,632,970) or reduction of adverse effects of photosensitizer or sonosensitizer (Sazgarnia et al., 2013).

BRIEF SUMMARY OF THE INVENTION

A first aspect of the invention comprises a method for damaging a target material in an organism, said method comprising: administering to the organism a composition comprising a sonosensitizing compound comprising at least one transition metal and three bidentate ligands; and exposing the sonosensitizing compound to an activating energy, wherein the target material comprises at least one of cells and microorganisms, and the activating energy comprises ultrasound effective to trigger the sonosensitizing compound to damage the target material.

In certain embodiments, the target material comprises hyperproliferating cells in the organism, and the method is effective to inhibit proliferation of the hyperproliferating cells in the organism or to destroy the hyperproliferating cells in the organism.

In certain embodiments, the target material comprises microorganisms selected from the group consisting of bacteria, viruses, and fungi, and the method is effective to destroy the microorganisms.

In certain embodiments, the organism is a human.

In certain embodiments, the composition is administered by topical, oral, buccal, intravenous, intramuscular, intraarterial, intramedullary, intrathecal, intraventricular, transdermal, subcutaneous, intraperitoneal, intranasal, enteral, topical, sublingual, vaginal, ophthalmic, pulmonary, rectal, or extracorporeal routes.

In certain embodiments, the composition is pharmaceutically acceptable and further comprises at least one pharmaceutically acceptable carrier, excipient, or diluent.

In certain embodiments, the composition further comprises a metal-binding glycoprotein, a glycated or non-glycated form thereof.

In certain embodiments, the metal-binding glycoprotein is transferrin.

In certain embodiments, the ultrasound is administered in a continuous fashion at 100% duty cycle.

In certain embodiments, the ultrasound is administered at a power of 0.01 W/cm$^2$ to 10 W/cm$^2$.

In certain embodiments, the ultrasound is administered in a pulsed fashion at a duty cycle between 5% and 95%.

In certain embodiments, the ultrasound is administered at a power of 10 W/cm$^2$ and frequency between 10 Hz to 10 MHz.

In certain embodiments, the sonosensitizing compound is administered in combination with electromagnetic radiation.

In certain embodiments, the combination of the sonosensitizing compound and the electromagnetic radiation is synergistically effective.

In certain embodiments, the electromagnetic radiation comprises infrared or visible light.

In certain embodiments, light is emitted from a laser.

In certain embodiments, the electromagnetic radiation comprises ionizing radiation.

In certain embodiments, the sonosensitizing compound has the formula (I):

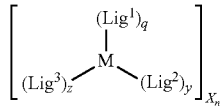

(I)

including hydrates, solvates, pharmaceutically acceptable salts, prodrugs and complexes thereof, wherein:

M is selected from the group consisting of osmium, ruthenium and rhodium;

X is selected from the group consisting of Cl$^-$, PF$_6^-$, Br$^-$, BF$_4^-$, ClO$_4^-$, CF$_3$SO$_3^-$, and SO$_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

q+y+z=3;

Lig$^1$ is a bidentate ligand that at each occurrence is each independently selected from the group consisting of

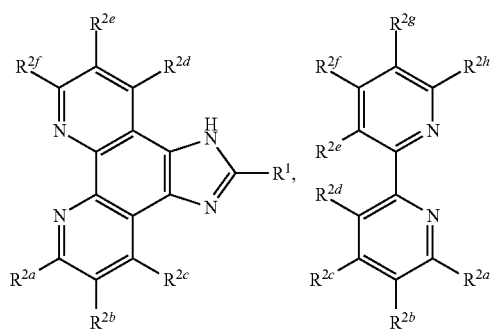

-continued

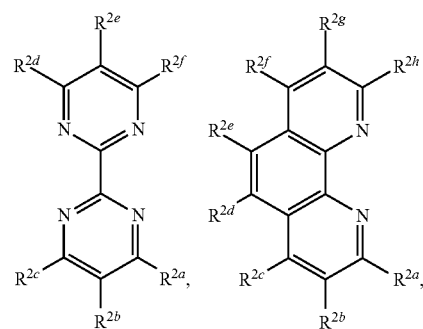

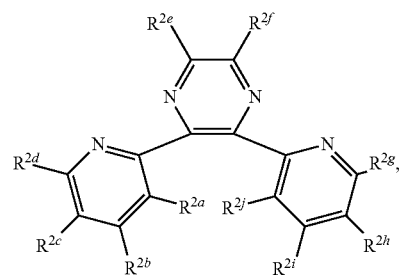

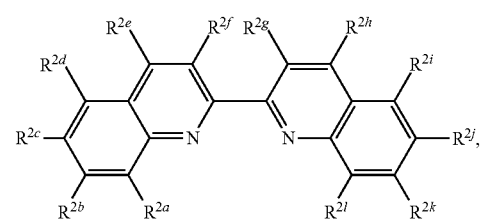

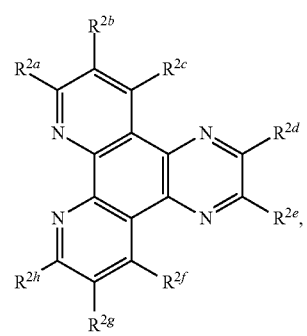

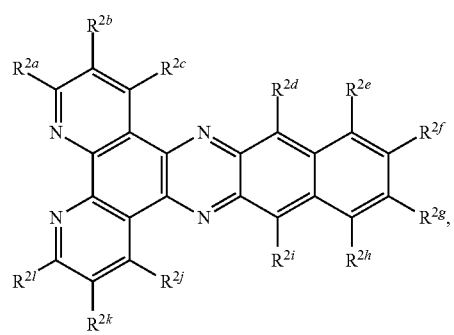

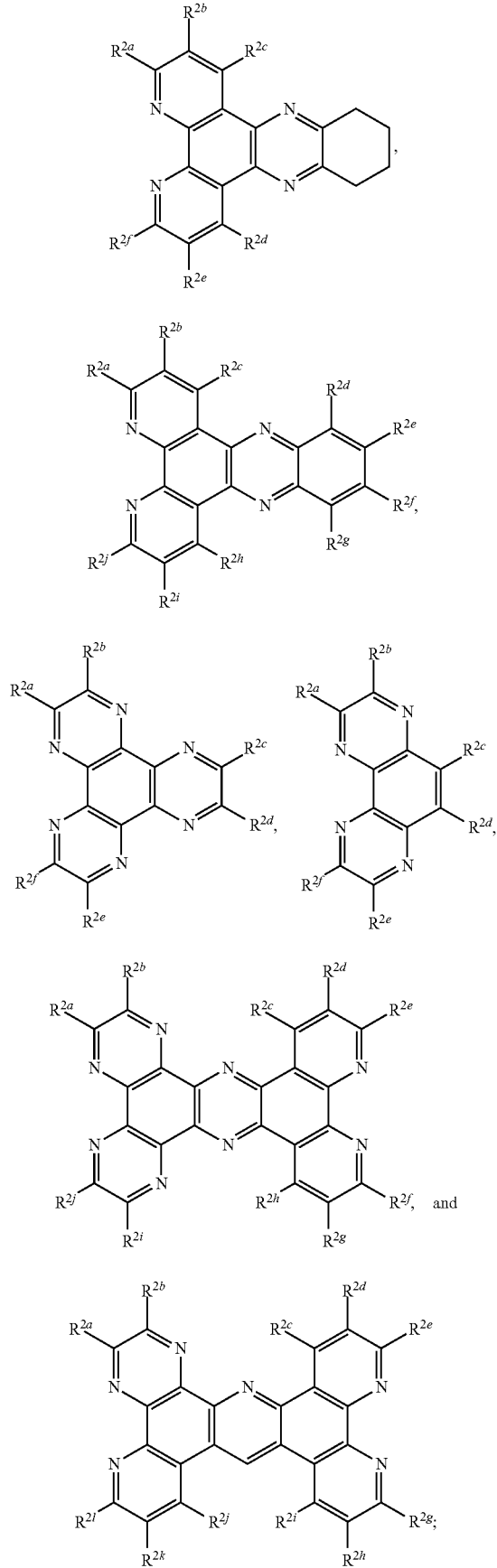
Lig² is a bidentate ligand that at each occurrence is each independently selected from the group consisting of -continued
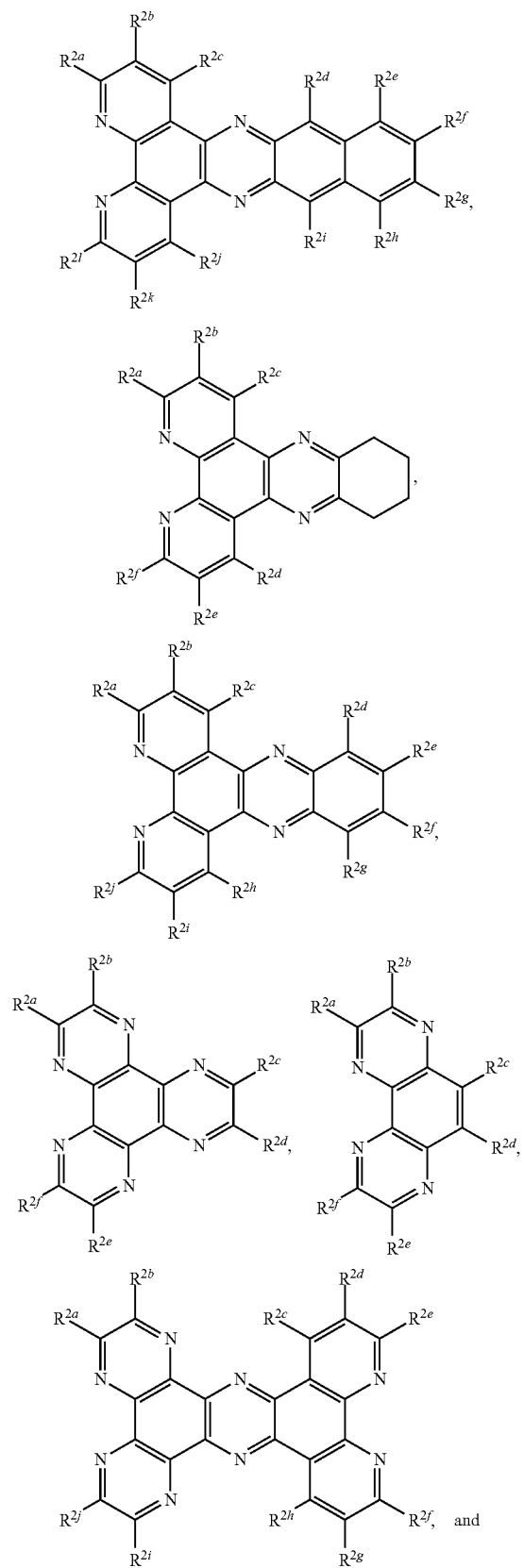
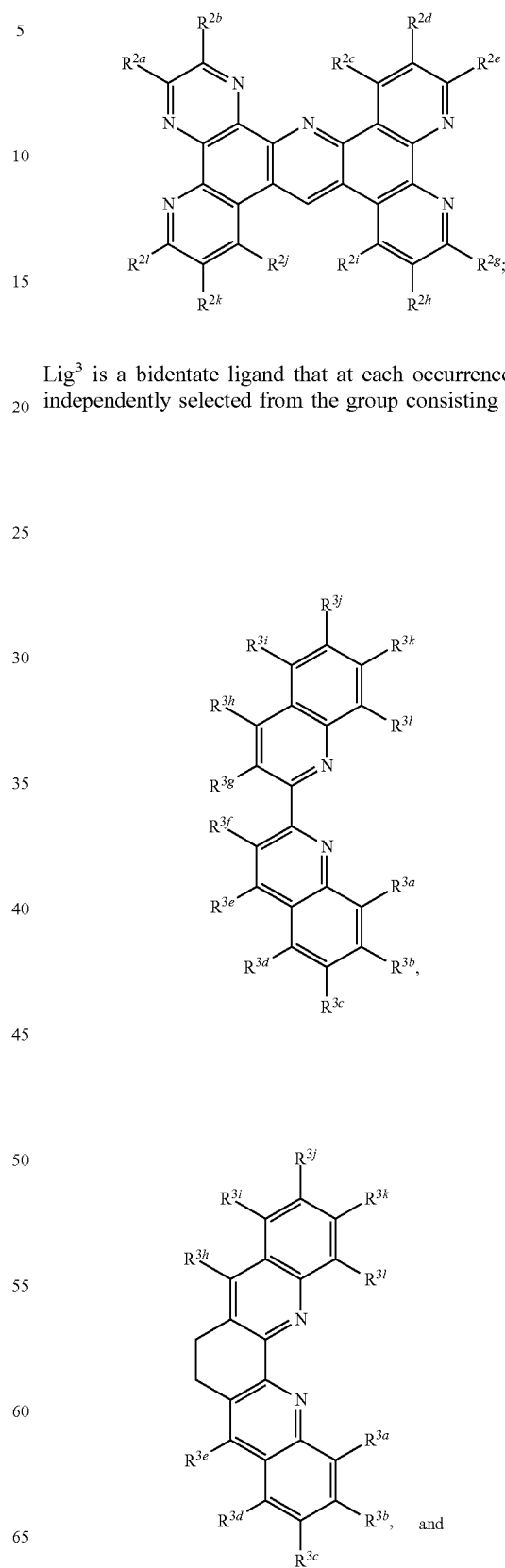
Lig³ is a bidentate ligand that at each occurrence is each independently selected from the group consisting of

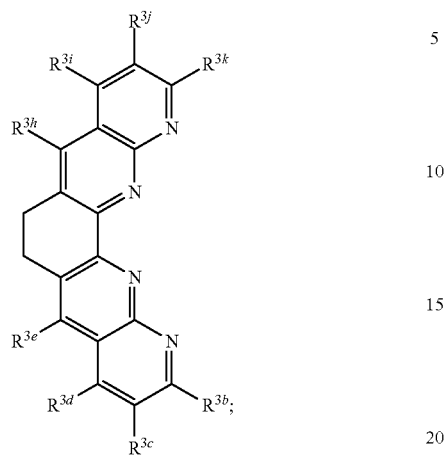
$R^1$ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
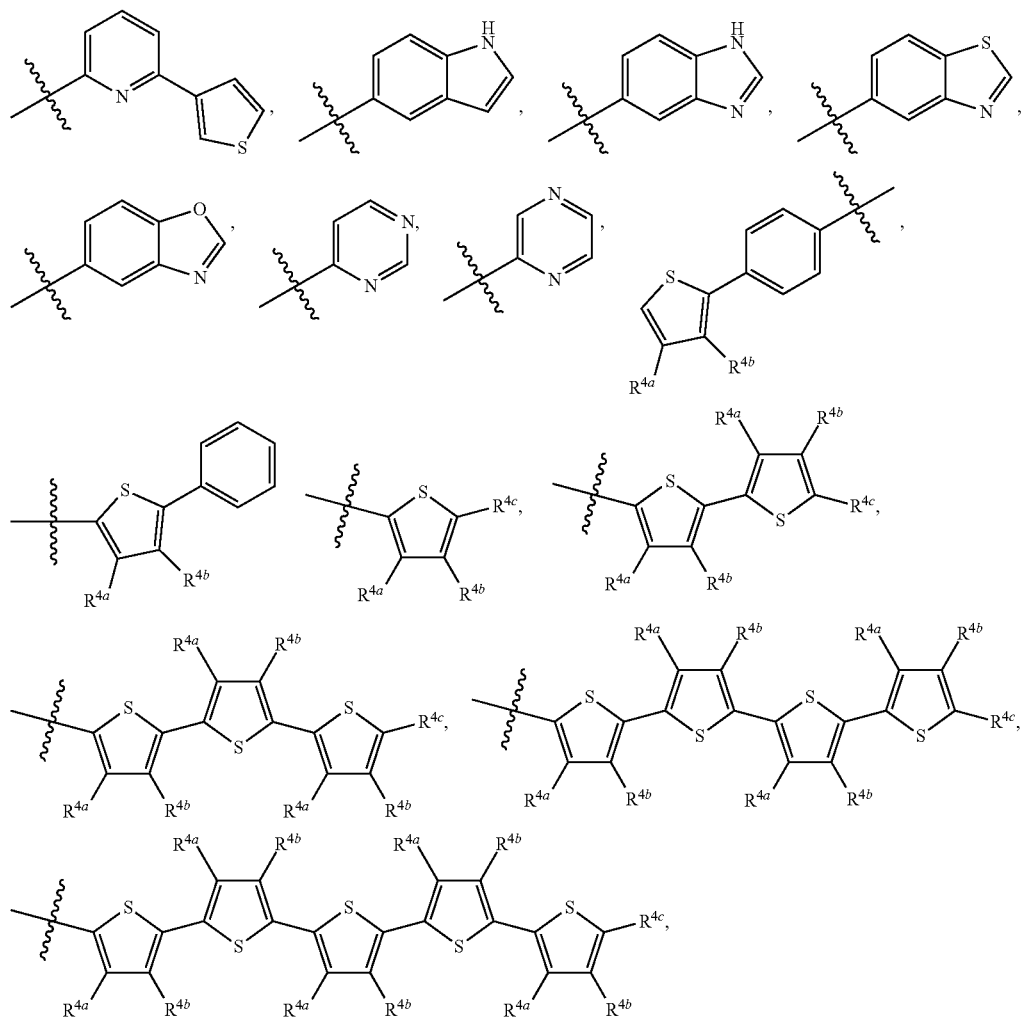

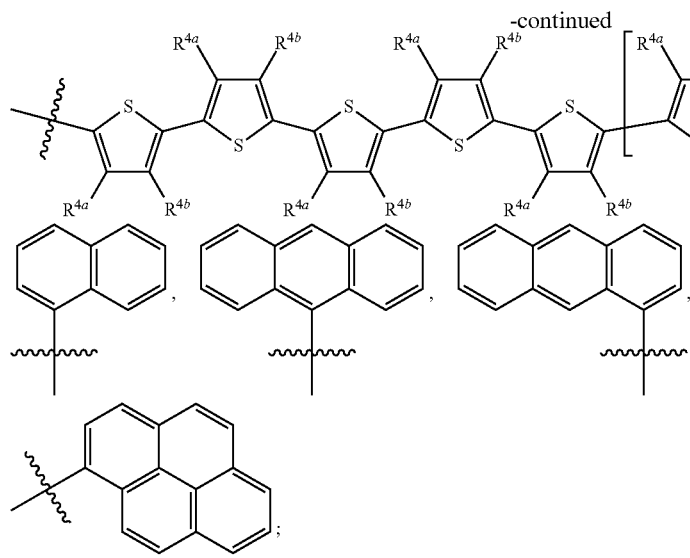

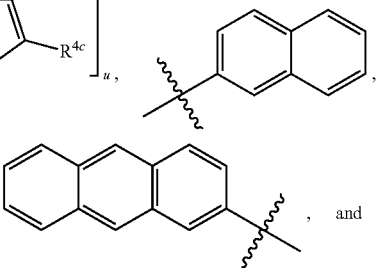
, and

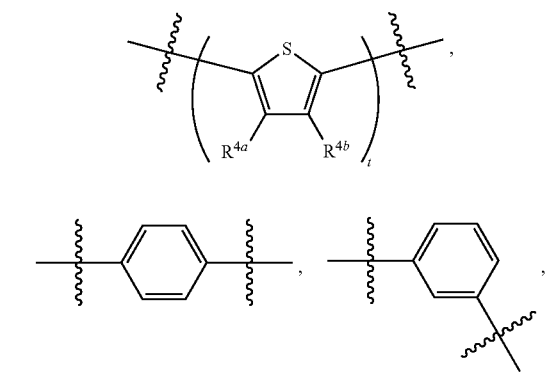
;

u is an integer from 1 to 10;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl.

In certain embodiments, the sonosensitizing compound has the formula (VI):

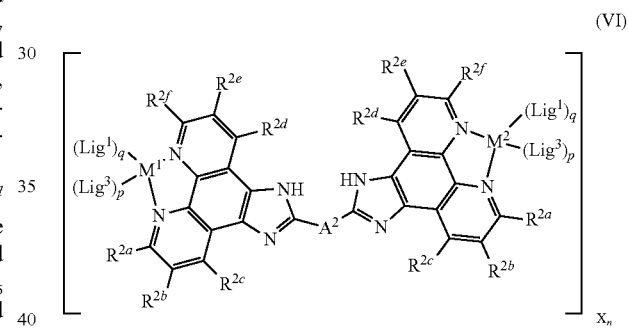

(VI)

including hydrates, solvates, pharmaceutically acceptable salts, prodrugs and complexes thereof wherein;

$M^1$ and $M^2$ at each occurrence is independently selected from the group consisting of osmium, manganese, molybdenum, rhenium, ruthenium, iron, cobalt, rhodium, iridium, nickel, platinum, and copper;

$A^2$ is selected from the group consisting of

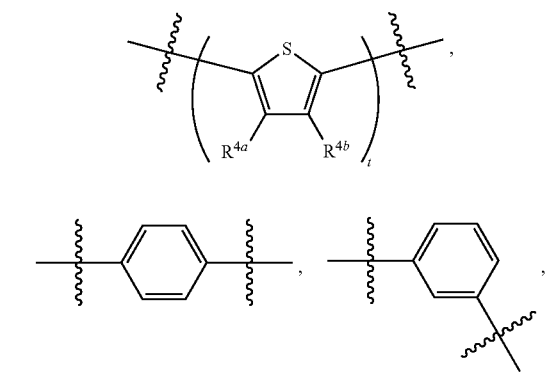

-continued

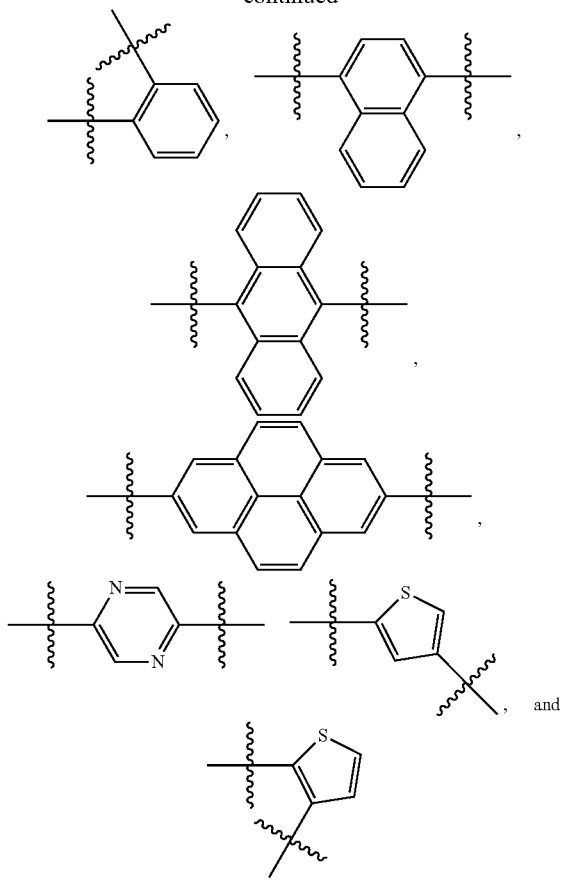

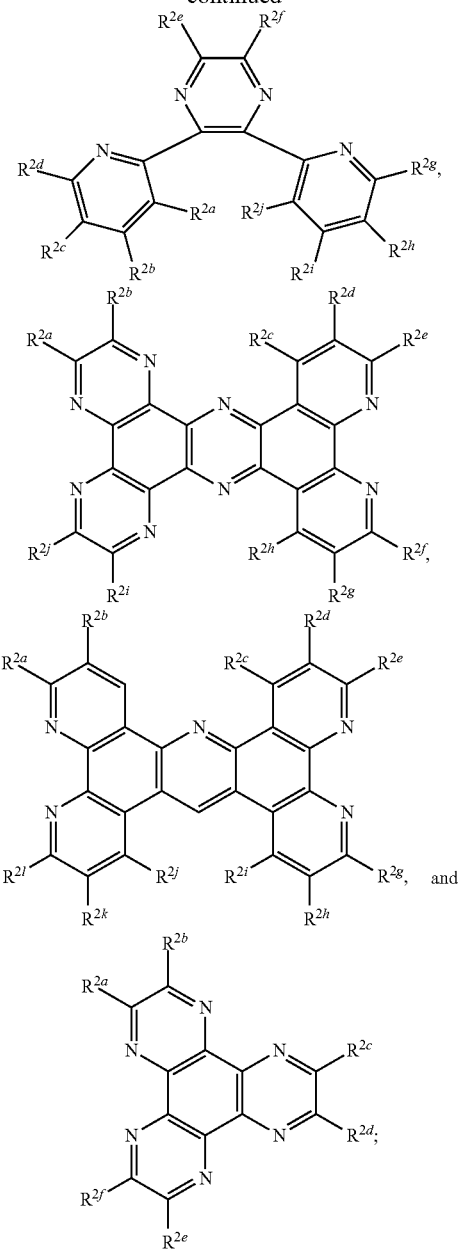

t is an integer.

In certain embodiments, the sonosensitizing compound has the formula (VIIa)

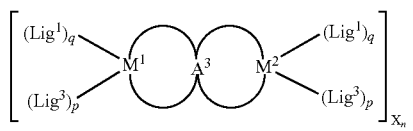

(VIIa)

including hydrates, solvates, pharmaceutically acceptable salts, prodrugs and complexes thereof wherein:

$A^3$ is selected from the group consisting of

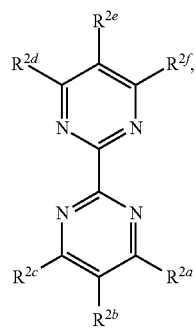

$Lig^1$ is a bidentate ligand that at each occurrence is each independently selected from the group consisting of

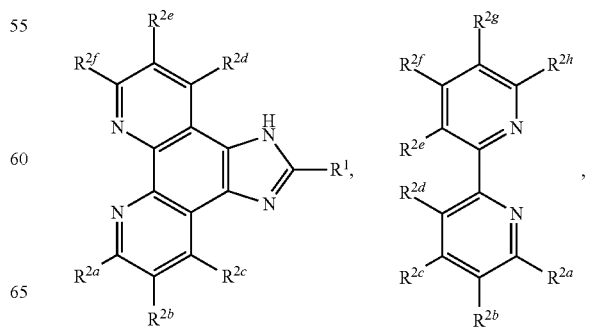

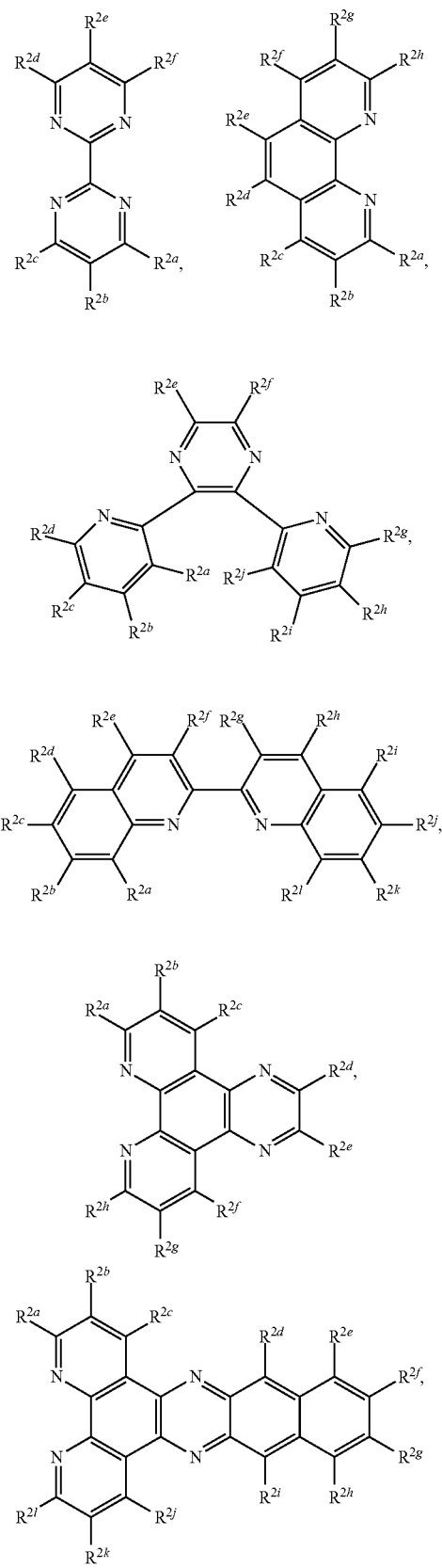
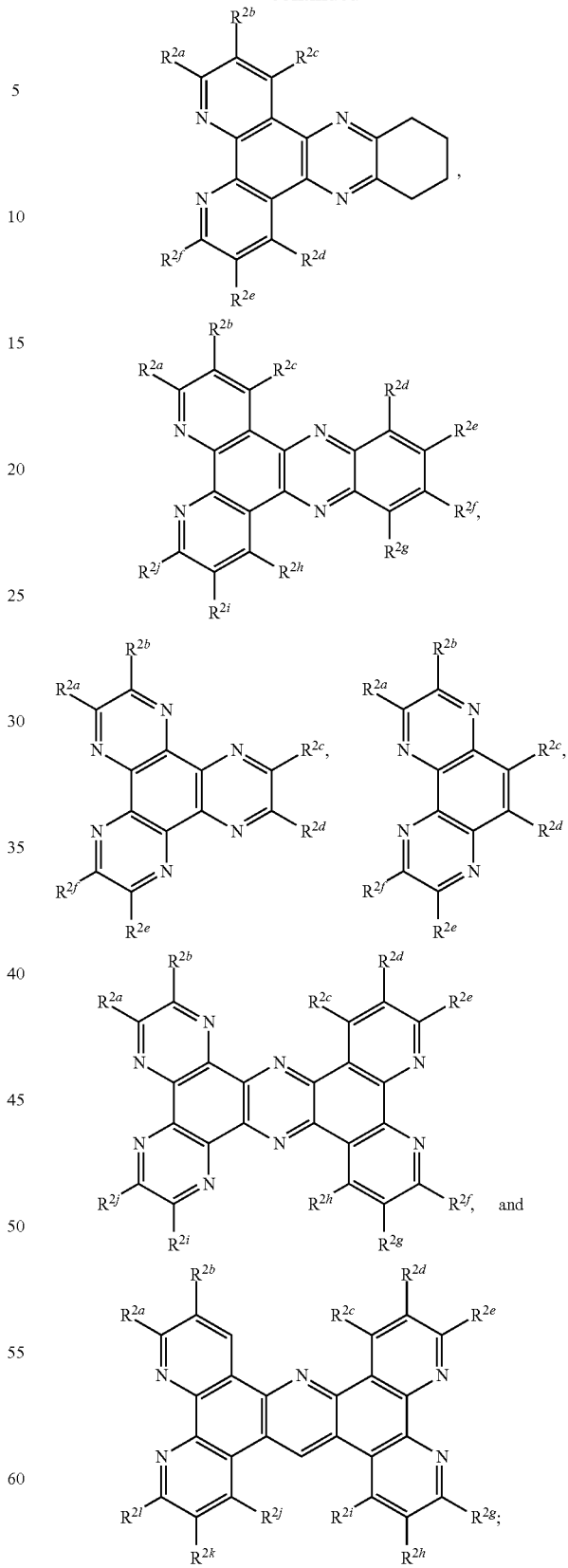
Lig³ is a bidentate ligand that at each occurrence is each independently selected from the group consisting of

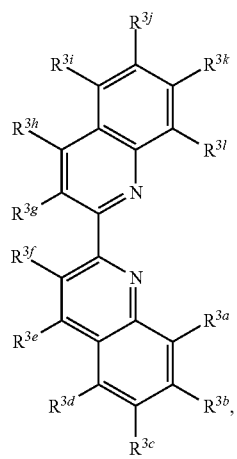
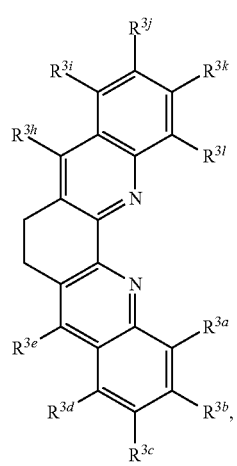
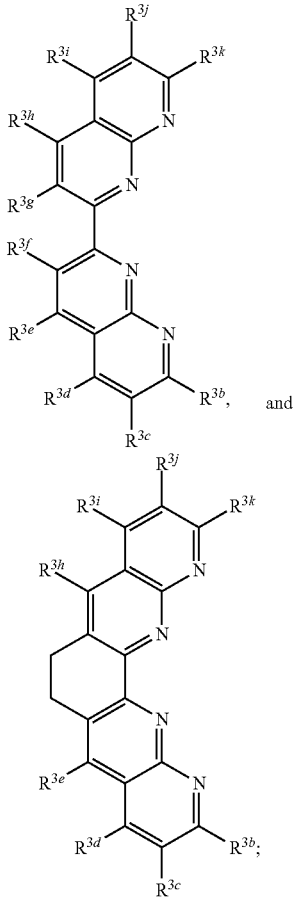
R[1] is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
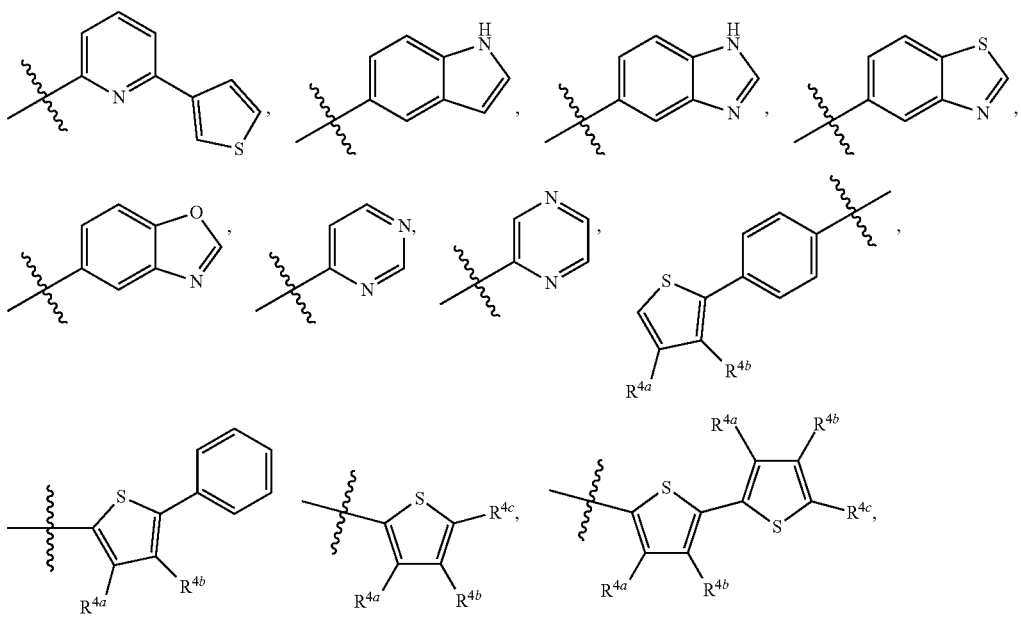

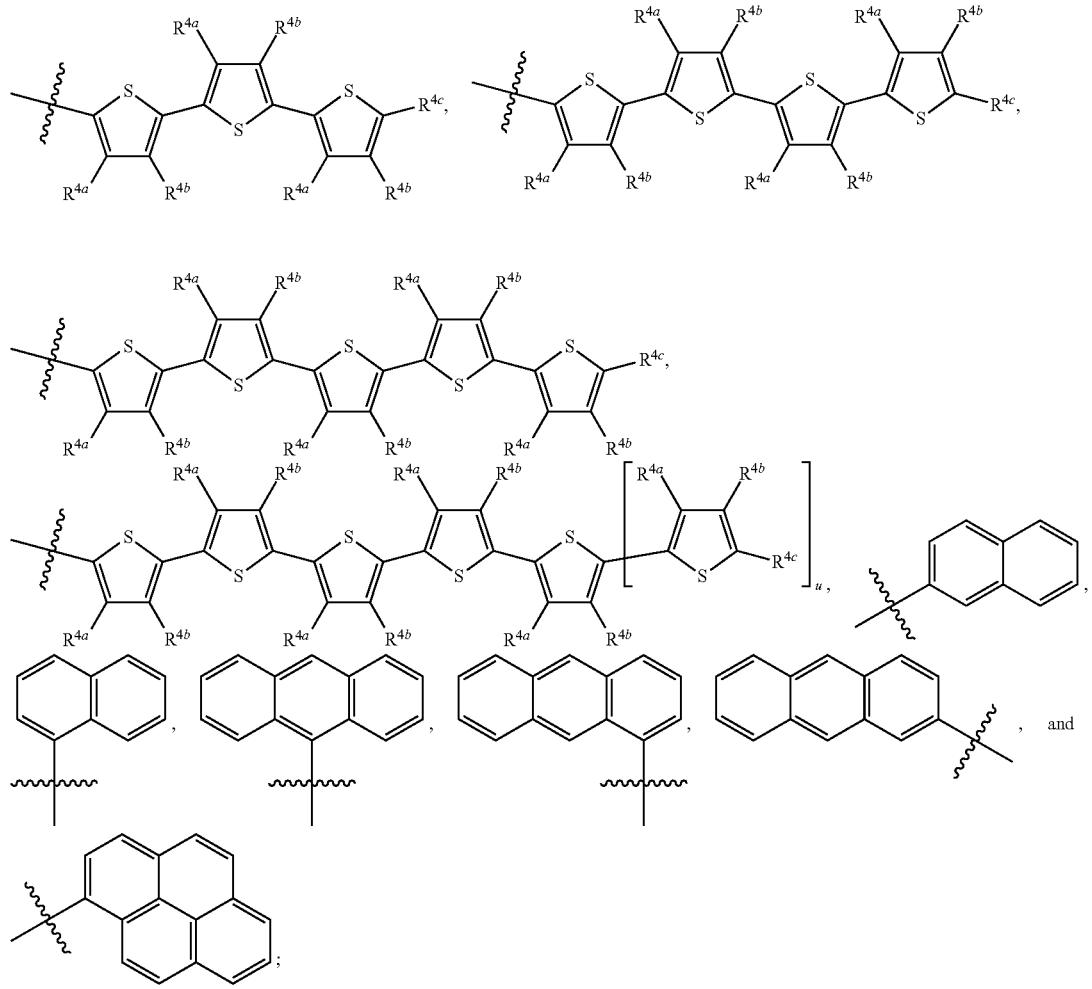

u is an integer from 1 to 10;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$ and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, and $R^{31}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl p is independently at each occurrence 0, 1, or 2;

q is independently at each occurrence 0, 1, or 2; and n is 0, 1, 2, 3, 4, or 5.

In certain embodiments, the sonosensitizing compound has the formula (II)

including hydrates, solvates, pharmaceutically acceptable salts, prodrugs and complexes thereof, wherein:

M is selected from the group consisting of manganese, molybdenum, rhenium, iron, ruthenium, osmium, cobalt, rhodium, iridium, nickel, platinum, and copper;

X is selected from the group consisting of Cl$^-$, PF$_6^-$, Br$^-$, BF$_4^-$, ClO$_4^-$, CF$_3$SO$_3^-$, and SO$_4^{-2}$;

n=0, 1, 2, 3, 4, or 5;

y=1, 2, or 3;

z=0, 1, or 2;

Lig at each occurrence is independently selected from the group consisting of

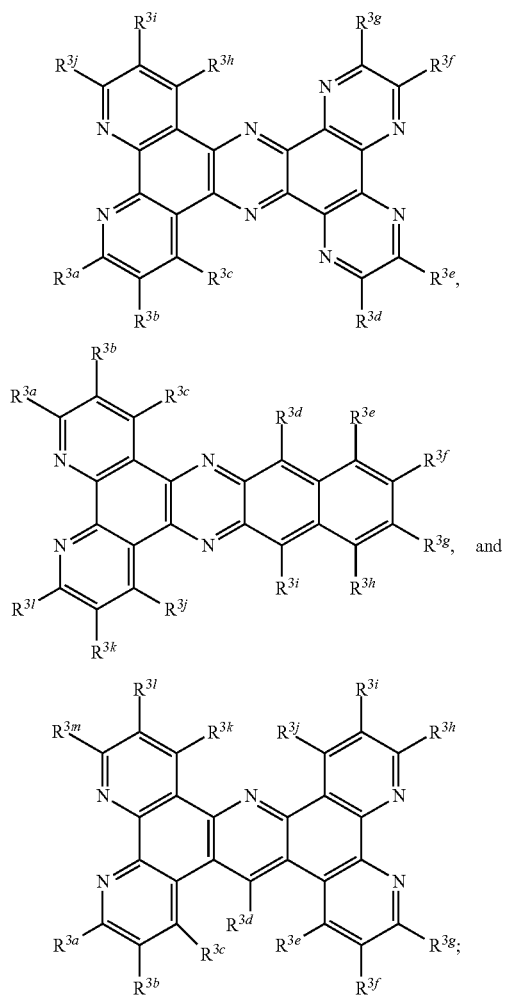

$R^1$ is selected from the group consisting of

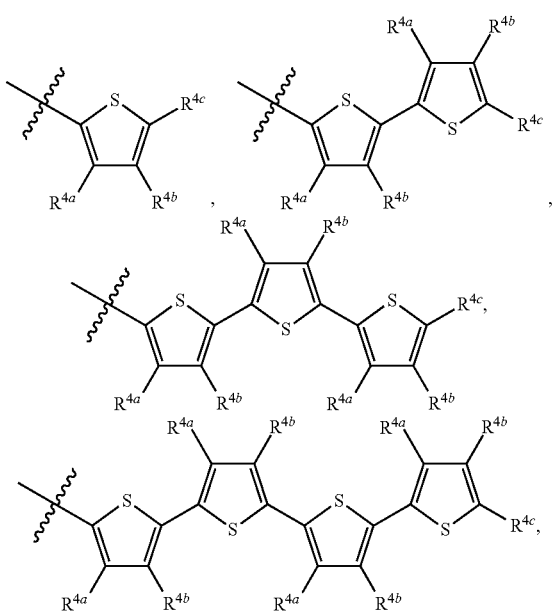

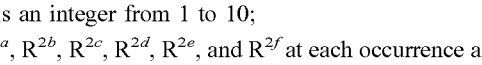

u is an integer from 1 to 10;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$, $R^{4b}$, and $R^{4c}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

In certain embodiments, the sonosensitizing compound has a structure selected from the group consisting of:

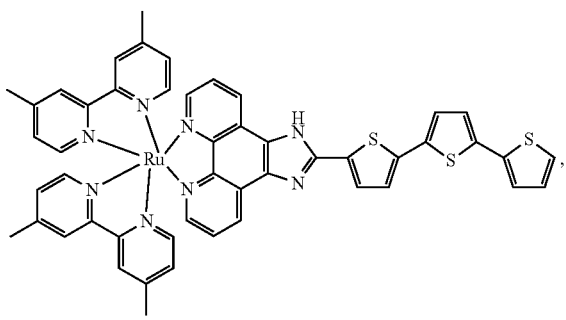

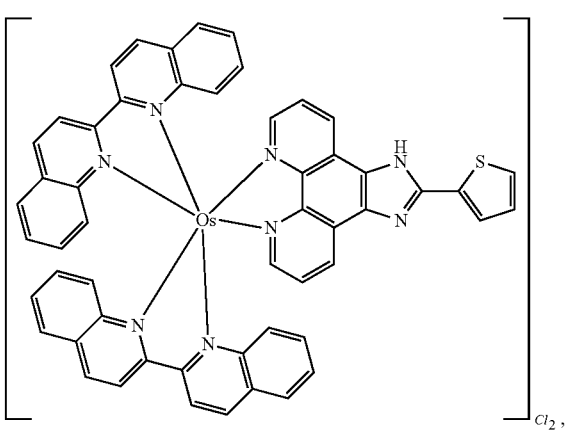

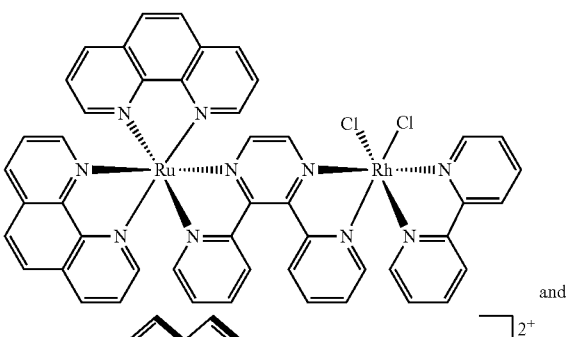

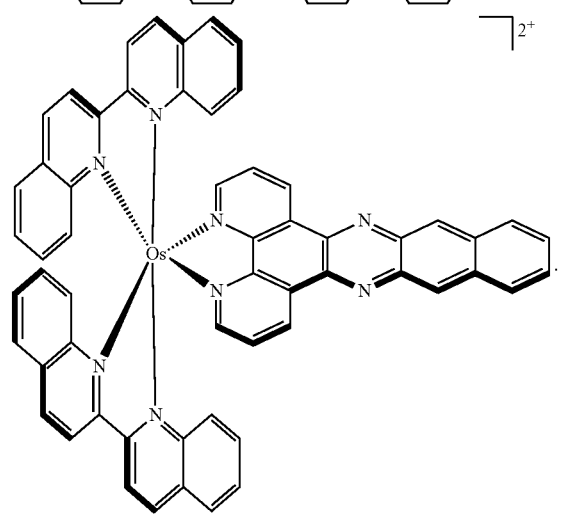

The invention encompasses any and all combinations of the embodiments individually set forth in this Summary of the Invention.

These and other objects, features, and advantages will become apparent to those of ordinary skill in the art from a reading of the following detailed descriptions and appended claims.

BRIEF DESCRIPTION OF THE DRAWINGS

The invention will be described in conjunction with the following drawings, wherein.

DETAILED DESCRIPTION OF PREFERRED EMBODIMENTS

Glossary

Figure 1A:
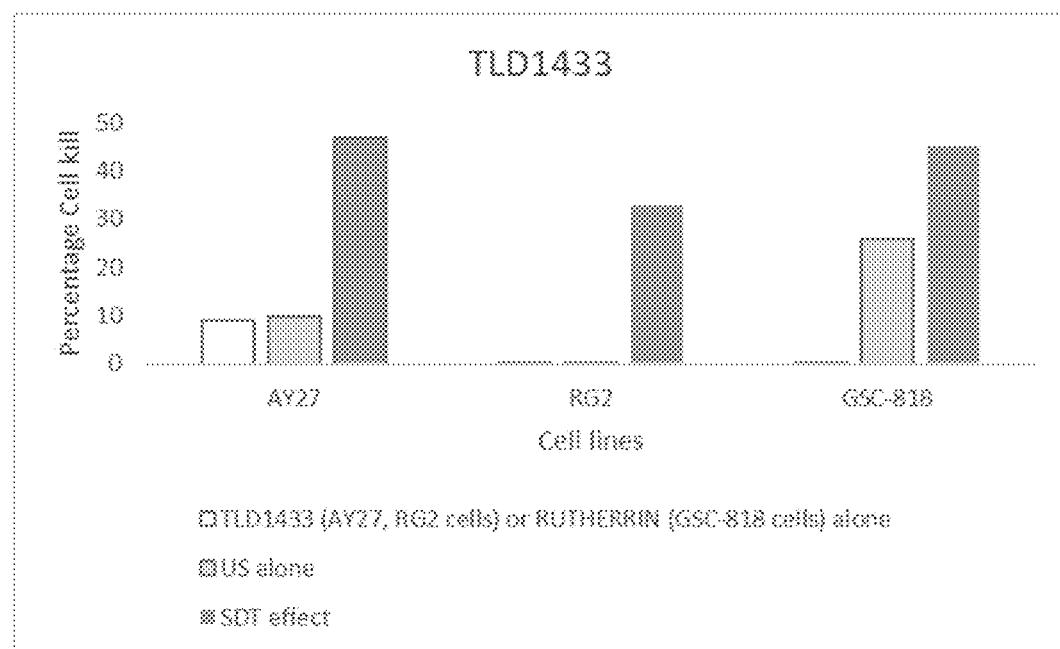
FIG. 1A is a bar graph of the percentage of AY27, RG2 and GSC-818 cells killed in vitro after exposure to: (a) the sonosensitizing agent TLD-1433 or RUTHERRIN (i.e., TLD-1433 plus transferrin); (b) ultrasound ("US"); or (c) the combination of TLD-1433 or RUTHERRIN and ultrasound ("SDT effect").

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

For the purposes of the present invention the terms "compound," "analog," and "composition of matter" stand equally well for the inventive compounds described herein, be they sonosensitizing or not, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO3, Na2CO3, KHCO3, K2CO3, Cs2CO3, LiOH, NaOH, KOH, NaH2PO4, Na2HPO4, and Na3PO4. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in N(R6)2, each R6 may be the same or different than the other). Combinations of substituents and/or variables are permissible only if such combinations result in stable compounds.

The terms "treat","treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "sonodynamic therapy" refers to a treatment for destroying cells or modulating immune function, including immune response, of cells and tissue through use of a sonosensitizing compound that can be activated by ultrasound of a certain dosage and intensity.

As used herein, the term "sonosensitizing compound" refers to a compound that provides sonodynamic therapy.

Except when noted, the terms "subject" or "patient" are used interchangeably and refer to mammals such as human patients and non-human primates, as well as other animals to be treated for experimental or clinical purposes, including but not limited to dogs, cats, rabbits, rats, and mice. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

As used herein, the term "biological target" refers to an organ, tissue and/or cell of an organism and/or to the organism itself.

As used herein, the term "electromagnetic radiation" refers to electromagnetic radiation of any wavelength or waveband.

All percentages, ratios and proportions herein are by weight, unless otherwise specified. All documents cited are in relevant part, incorporated herein by reference; the citation of any document is not to be construed as an admission that it is prior art with respect to the present invention.

Method of the Invention

The method of the present invention is effective to: (a) inhibit proliferation of hyperproliferating cells in an organism; (b) destroy hyperproliferating cells in an organism; and/or (c) destroy targeted microorganisms in an organism or other medium.

Hyperproliferating cells are cells which have an abnormally high rate of cell division. Such cells include but are not limited to tumor or cancer cells (including but not limited to leukemia cells, ovarian cancer cells, Burkitt's lymphoma cells, breast cancer cells, gastric cancer cells, testicular cancer cells, melanoma cells and the like), and cells associated with psoriasis, warts, macular degeneration and other non-malignant hyperproliferating conditions. Thus, the method of the invention is useful for treating conditions associated with hyperproliferating cells, such as cancer, psoriasis, warts and/or macular degeneration.

Microorganisms targeted for destruction by the method of the invention include but are not limited to bacteria, viruses and fungi. Thus, embodiments of the inventive method are useful for disinfection, sterilization and/or treatment of conditions associated with bacterial, viral and/or fungal infection.

The method can be performed in vitro or in vivo, as well as extracorporeally. Biological targets of the invention are organisms, organs, tissues and/or cells amenable to treatment by the method of the invention. Organisms in which the method can be performed include but are not limited to microorganisms, including varieties of microscopic organisms, warm-blooded and cold-blooded animals, particularly mammals, and most particularly humans.

The method of the invention comprises administering to the organism a composition comprising a sonosensitizing compound containing at least one transition metal. Unlike US 20030082101, the sonosentizing compound further comprises three bidentate ligands complexed to the at least one transition metal. The mode of administration is not particularly limited. In certain embodiments, the composition can be administered by topical, oral, buccal, intravenous, intramuscular, intra-arterial, intramedullary, intrathecal, intraventricular, transdermal, subcutaneous, intraperitoneal, intranasal, enteral, sublingual, vaginal, ophthalmic, pulmonary, or rectal routes. The composition can also be administered extracorporeally.

In certain embodiments, the composition further comprises a metal-binding glycoprotein or a metal-binding nonglycated protein and/or their recombinants. In preferred embodiments, the metal-binding glycoprotein is transferrin or its recombinant.

After the sonosensitizing compound is administered to the organism, the tissues exposed to the compound become sensitized. The sensitized tissues are then exposed to ultrasound. In certain embodiments, the ultrasound is administered at a power of 0.1, 0.2, 0.3, 0.4, 0.5, 0.6, 0.7, 0.8, or 0.9 W/cm² to 1.0, 1.5, 2.0, 2.5, 3.0, 5.0, 7.5, or 10W/cm². In certain embodiments, ultrasound is administered at 100% duty cycle which causes the ultrasound to be administered in a continuous fashion. For 100% duty cycle administration, ultrasound is administered at a power between 0.1 W/cm² and 10 W/cm². In preferred embodiments, ultrasound is administered at a duty cycle between 5% and 95%, allowing ultrasound to be administered in a pulsed fashion. For pulsed ultrasound administration, ultrasound is administered at a power of 10 kW/cm² and a frequency between 10 Hz and 10 MHz.

The dosage of ultrasound is preferably safe and effective to inhibit proliferation of hyperproliferating cells, destroy hyperproliferating cells, and/or destroy targeted microorganisms. Factors relevant to determining a suitable dosage include the pulse ratio, intensity, depth of the target (e.g.: cells, tissues, organs, anatomical sites, etc.), and other factors. It is preferred that the ultrasound dosage be insufficient to raise the temperature of the tissue being targeted or raise said temperature to 40° C. or less).

In preferred embodiments, the organism is exposed to a combination of ultrasound and electromagnetic radiation in an order and at a power which are synergistically effective to achieve at least one of the following results: (a) inhibiting proliferation of hyperproliferating cells in the organism; (b) destroying hyperproliferating cells in the organism; and (c) destroying targeted microorganisms in the organism and/or extracorporeally. In certain embodiments, the electromagnetic radiation comprises photodynamic therapy, radiation, and low level laser therapy. Synergistic efficacy is established by showing that the cell kill percentage resulting from the combined application of ultrasound and electromagnetic radiation is greater than the sum of the cell kill percentages resulting from the independent application of ultrasound and electromagnetic radiation.

Sonosensitizing compounds suitable for use in the invention can be prepared in accordance with the procedures outlined herein, from commercially available starting materials, compounds known in the literature, or readily prepared intermediates, by employing standard synthetic methods and procedures known to those skilled in the art.

Suitable sonosensitizing compounds preferably contain at least one transition metal, which is preferable a Group 8 or 9 metal, such as Fe, Ru, Os, Co, Rh, and Ir, and is most preferably at least one of Ru, Rh, and Os.

In certain embodiments, the sonosensitizing compounds comprise a transition metal complexed with three bidentate ligands.

In certain embodiments, the sonosensitizing compound has the formula

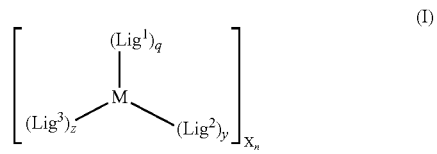

including hydrates, solvates, pharmaceutically acceptable salts, prodrugs and complexes thereof, wherein:

M at each occurrence is independently a transition metal, which is preferably selected from the group consisting of osmium, ruthenium and rhodium;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

$Lig^1$ is a bidentate ligand that at each occurrence is each independently selected from the group consisting of

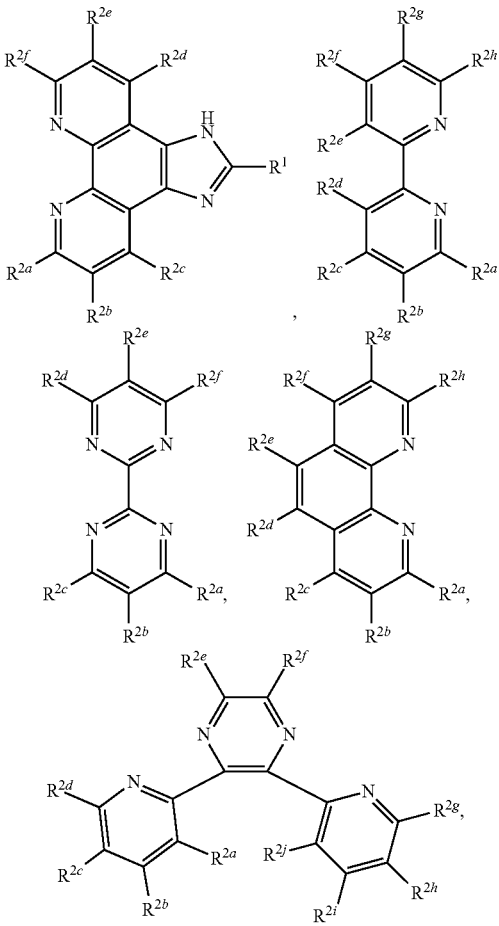

-continued
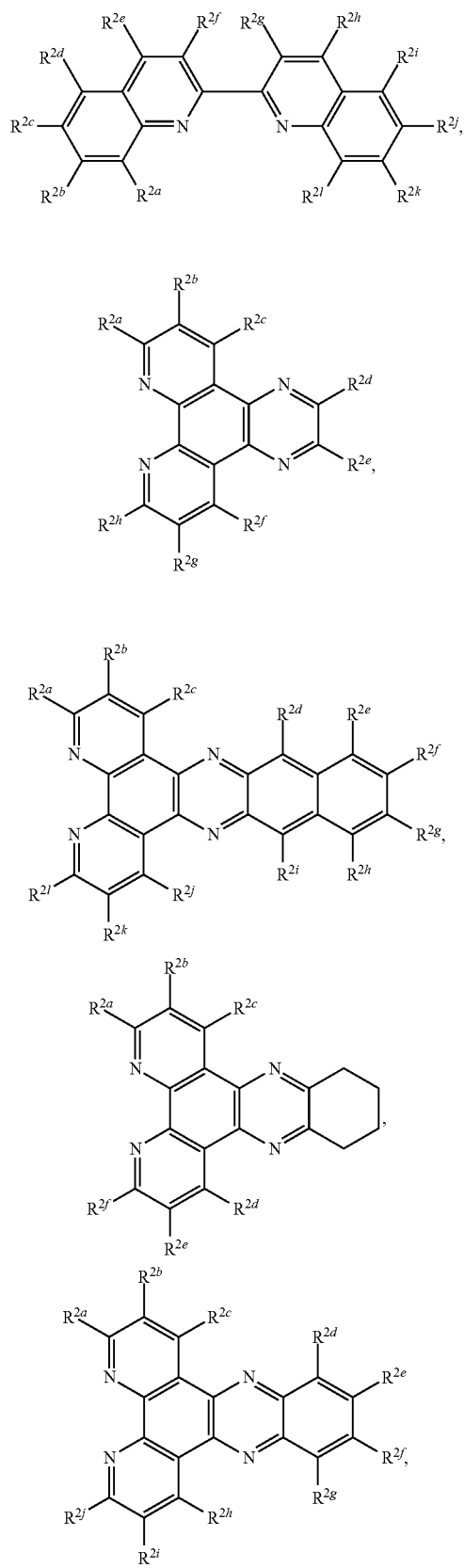
-continued
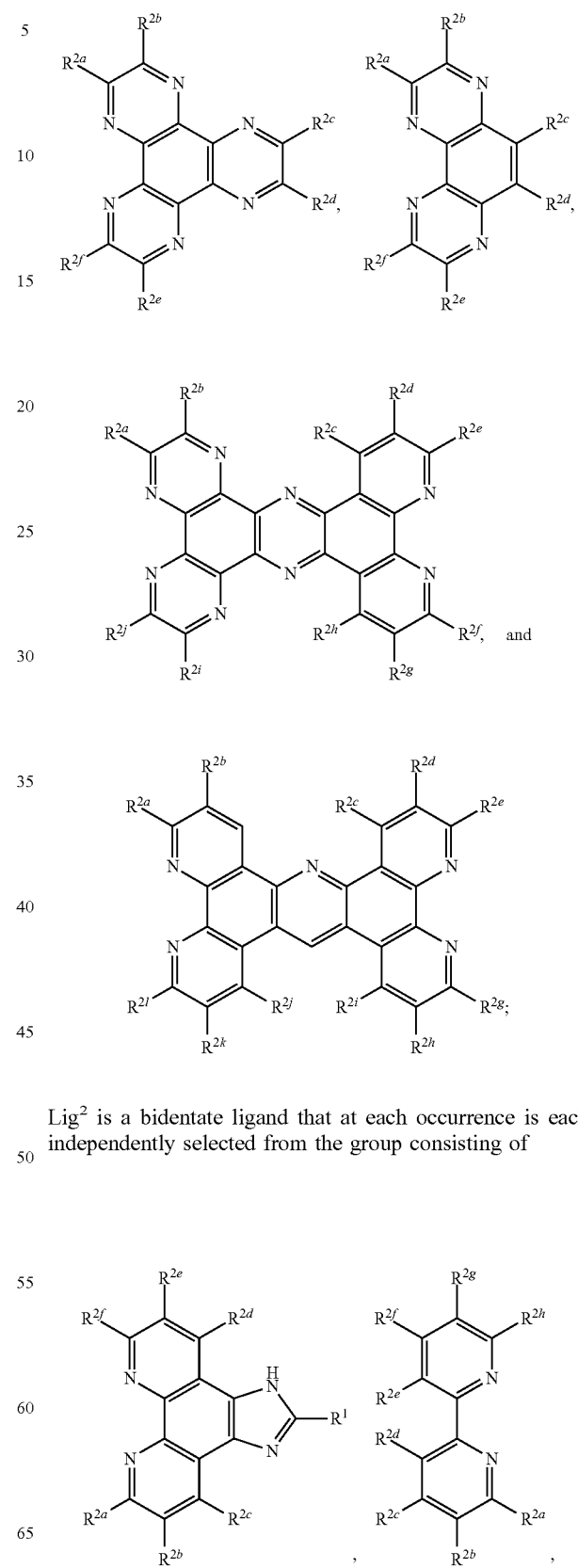
Lig² is a bidentate ligand that at each occurrence is each independently selected from the group consisting of

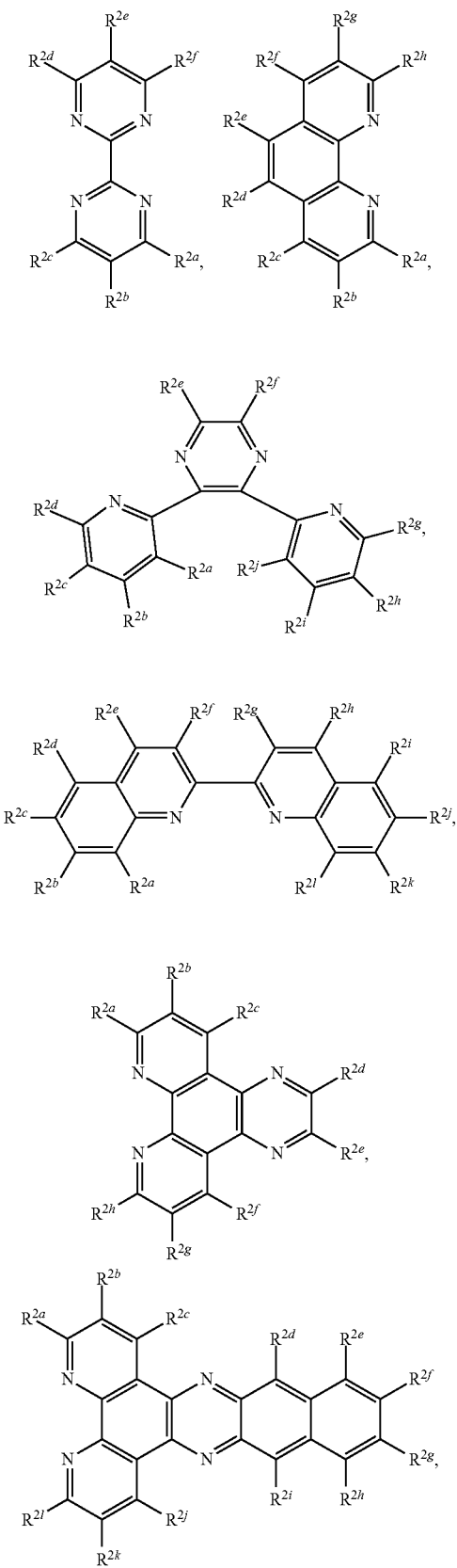
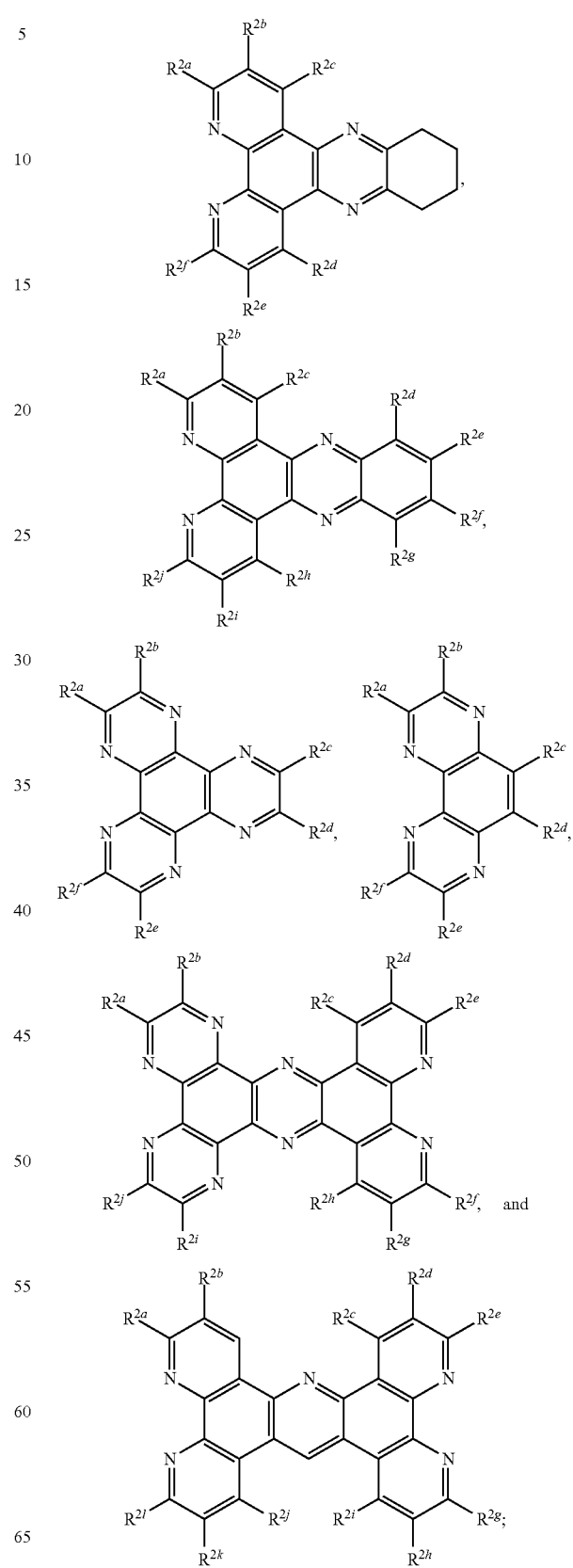

Lig³ is a bidentate ligand that at each occurrence is each independently selected from the group consisting of
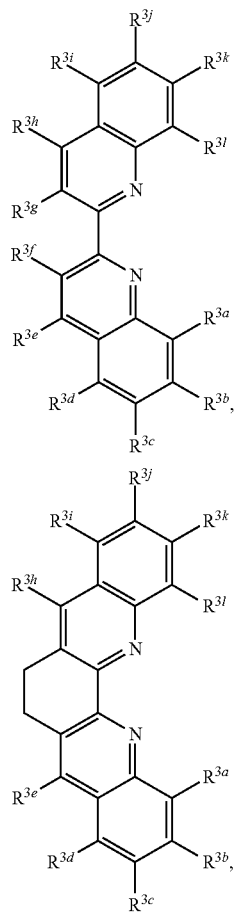
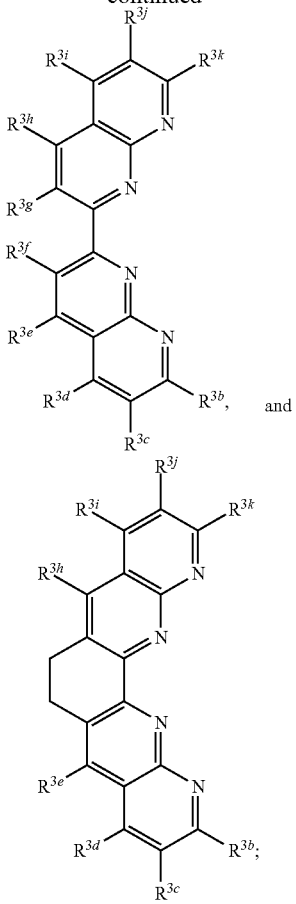
R¹ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
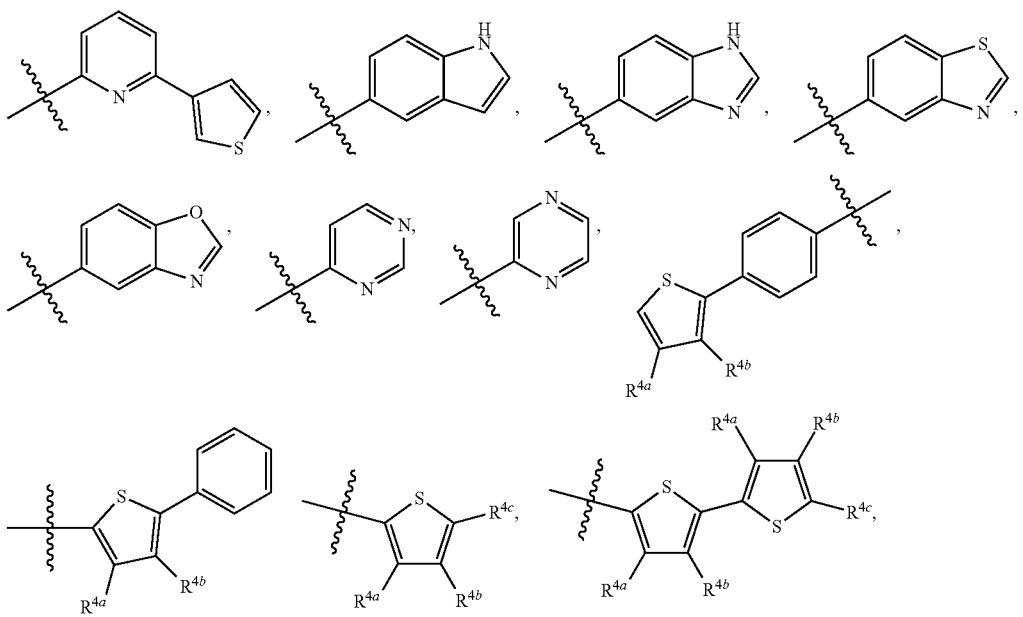

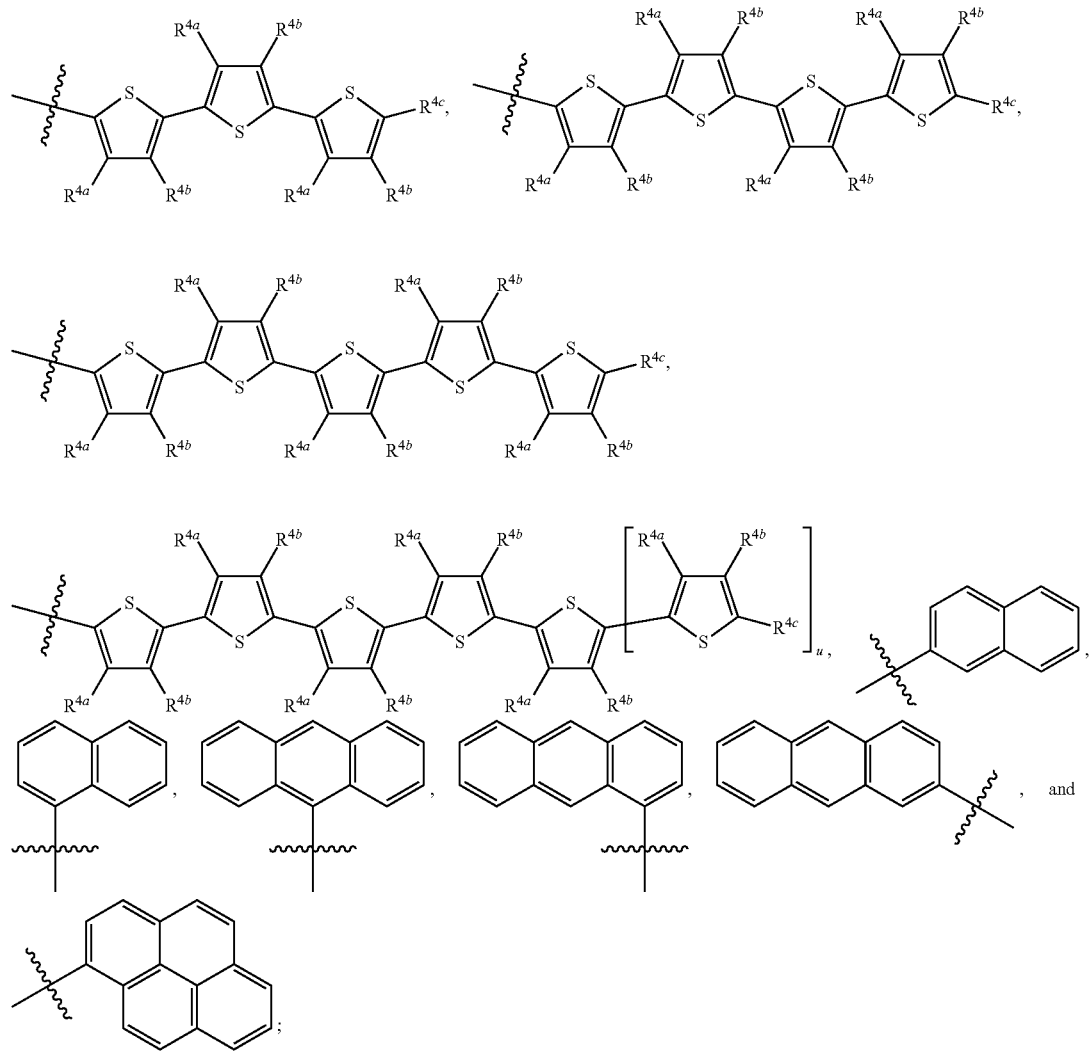

u is an integer from 1 to 10;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ and $R^{31}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$ sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl.

In certain embodiments, the sonosensitizing compound has the formula (VI):

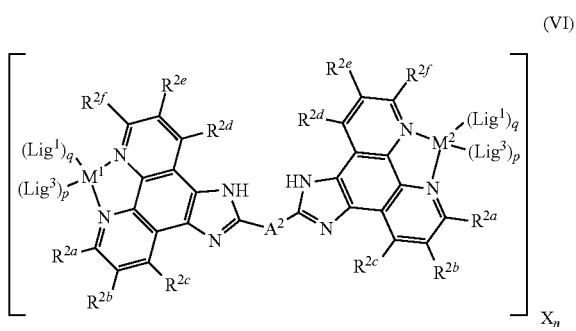

(VI)

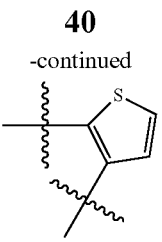

including hydrates, solvates, pharmaceutically acceptable salts, prodrugs and complexes thereof wherein;

$M^1$ and $M^2$ at each occurrence is independently a transition metal, and is preferably independently selected from the group consisting of osmium, manganese, molybdenum, rhenium, ruthenium, iron, cobalt, rhodium, iridium, nickel, platinum, and copper;

$A^2$ is selected from the group consisting of

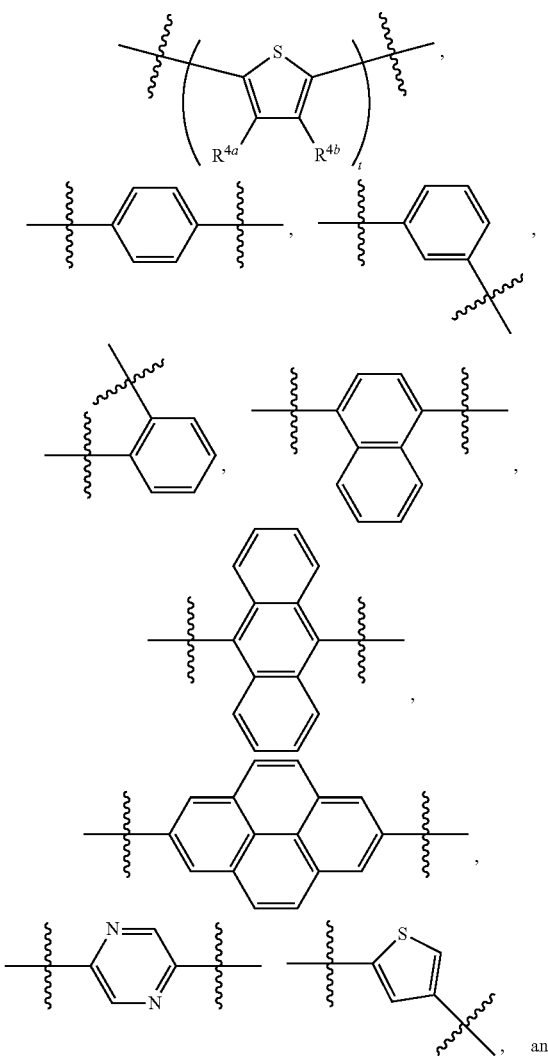

, and t is an integer.

In certain embodiments, the sonosensitizing compound has the formula (VIIa)

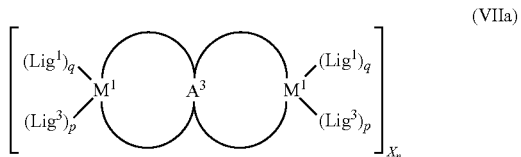

(VIIa)

including hydrates, solvates, pharmaceutically acceptable salts, prodrugs and complexes thereof wherein:

$M^1$ and $M^2$ at each occurrence is independently a transition metal, and is preferably independently selected from the group consisting of osmium, manganese, molybdenum, rhenium, ruthenium, iron, cobalt, rhodium, iridium, nickel, platinum, and copper;

$Lig^1$ is a bidentate ligand that at each occurrence is each independently selected from the group defined above;

$Lig^3$ is a bidentate ligand that at each occurrence is each independently selected from the group defined above;

p is independently at each occurrence 0, 1, or 2;

q is independently at each occurrence 0, 1, or 2;

n is 0, 1, 2, 3, 4, or 5; and $A^3$ is selected from the group consisting of

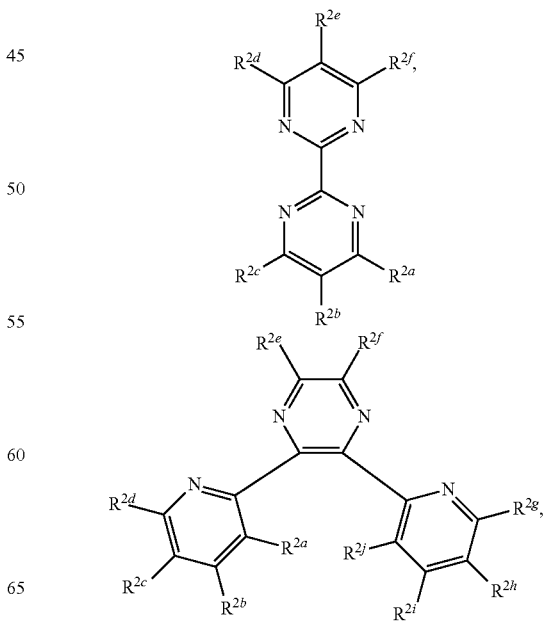

-continued

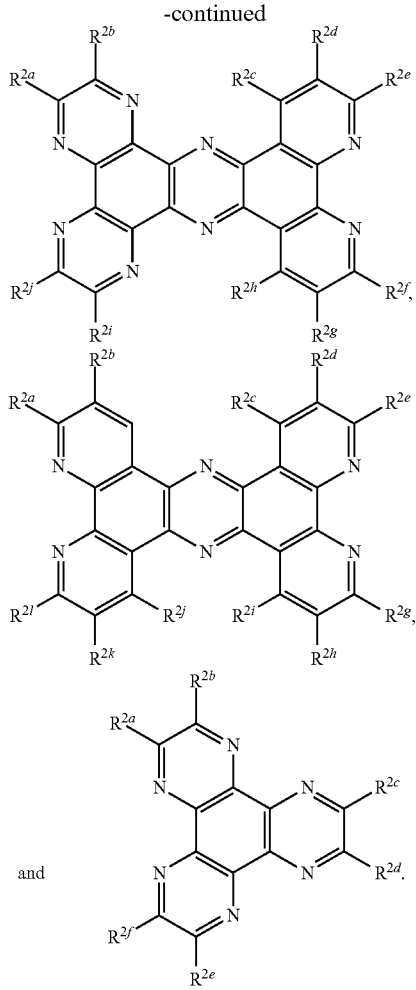

and

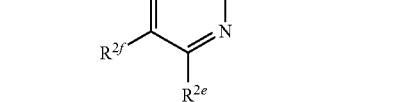

In certain embodiments, the sonosensitizing compound has the formula (II)

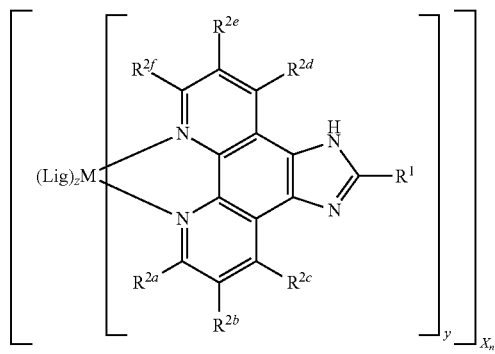

including hydrates, solvates, pharmaceutically acceptable salts, prodrugs and complexes thereof, wherein:
M is a transition metal preferably selected from the group consisting of manganese, molybdenum, rhenium, iron, ruthenium, osmium, cobalt, rhodium, iridium, nickel, platinum, and copper;
X is selected from the group consisting of Cl$^-$, PF$_6^-$, Br$^-$, BF$_4^-$, ClO$_4^-$, CF$_3$SO$_3^-$, and SO$_4^{-2}$;
n=0, 1, 2, 3, 4, or 5;
y=1, 2, or 3;
z=0, 1, or 2;
Lig at each occurrence is independently selected from the group consisting of

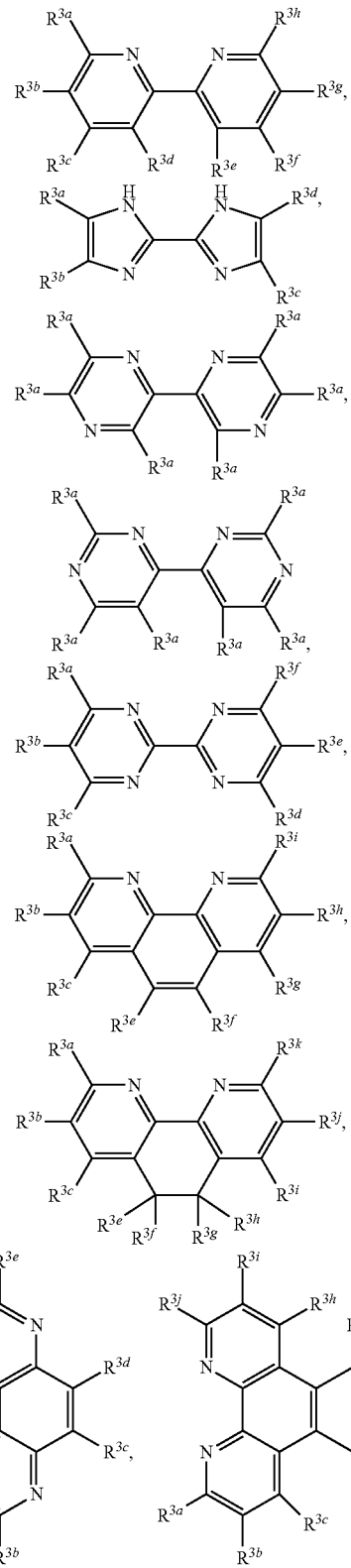

-continued
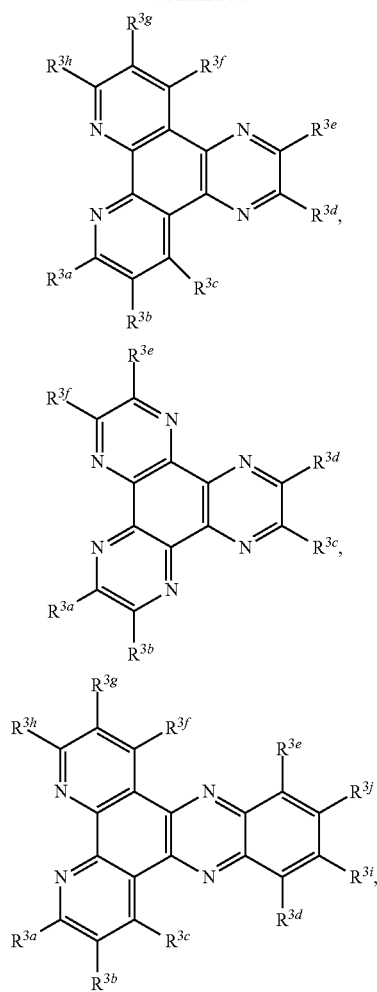
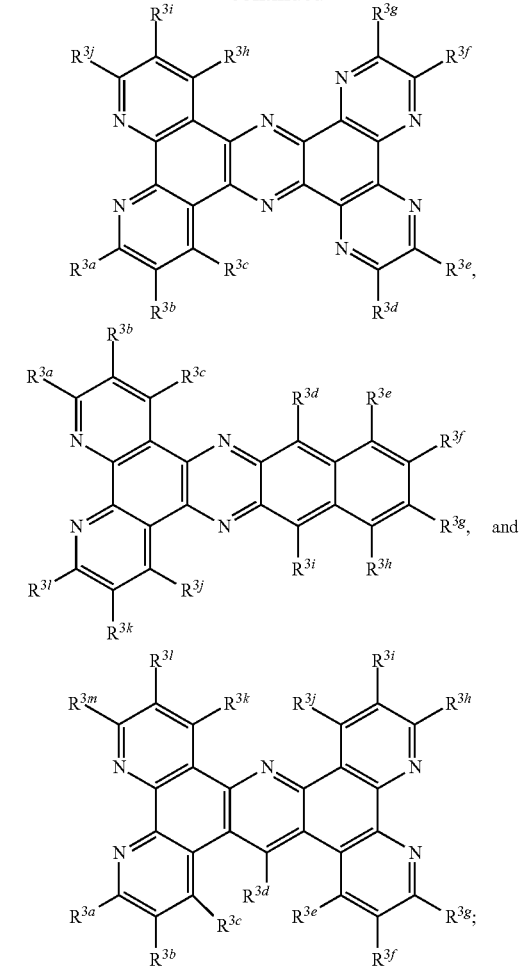
and
$R^1$ is selected from the group consisting of
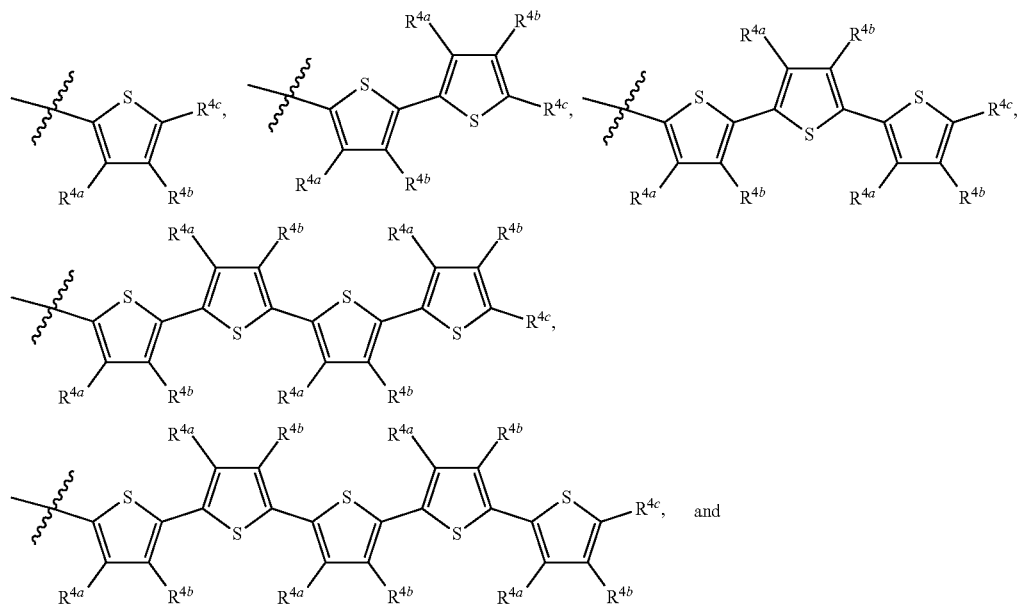
and -continued

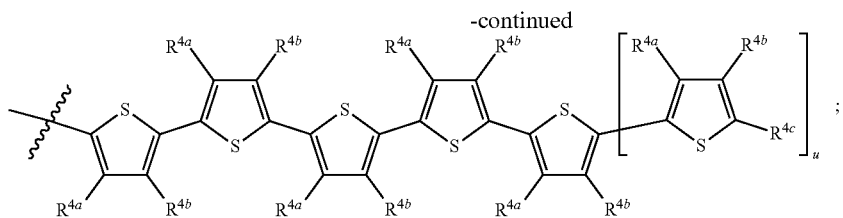

u is an integer from 1 to 10;

$R^{2a}$, $R^{2b}$, $R^{2c}$, $R^{2d}$, $R^{2e}$, and $R^{2f}$ at each occurrence are each independently selected from the group consisting of hydrogen, C1-6 optionally substituted alkyl, C1-6 optionally substituted branched alkyl, C3-7 optionally substituted cycloalkyl, C 1-6 optionally substituted haloalkyl, C1-6 optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$ $R^{3i}$, $R^{3j}$, $R^{3k}$, $R^{3l}$, and $R^{3m}$ at each occurrence are each independently selected from the group consisting of hydrogen, C1-6 optionally substituted alkyl, C1-6 optionally substituted branched alkyl, C1-6 optionally substituted haloalkyl, C1-6 optionally substituted alkoxy, and $CO_2R^8$;

$R^{4a}$, $R^{4b}$, and $R^{4c}$ at each occurrence are each independently selected from the group consisting of hydrogen, C1-6 optionally substituted alkyl, C1-6 optionally substituted branched alkyl, C1-6 optionally substituted cycloalkyl, C1-6 optionally substituted haloalkyl, C1-6 optionally substituted alkoxy, $CO_2R^5$, $CONR^6{}_2$, $NR^7{}_2$ , sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence is independently selected from the group consisting of hydrogen and optionally substituted alkyl;

$R^6$ at each occurrence is independently selected from the group consisting of hydrogen and optionally substituted alkyl;

$R^7$ at each occurrence is independently selected from the group consisting of hydrogen and optionally substituted alkyl; and $R^8$ at each occurrence is independently selected from the group consisting of hydrogen and optionally substituted alkyl.

In all of the embodiments provided herein, suitable optional substituents are not intended to limit the scope of the claimed invention. The sonosensitizing compounds may contain any of the substituents, or combinations of substituents, provided herein.

Preferred embodiments of the invention comprise an effective amount of at least one sonosensitizing compound to inhibit proliferation of hyperproliferating cells, and at least one excipient or carrier. For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

In preferred embodiments, sonosensitizing compound containing compositions further comprise a metal-binding glycoprotein (preferably transferrin) and/or its non-glycated recombinant protein as a delivery vehicle for metal-based sonosensitizing compounds, so as to facilitate delivery of the sonosensitizing compounds into a biological target.

In certain embodiments, a combination of different transition metal sonosensitizing compounds can be used. At least one, more than one or all of the different sonosensitizing compounds are preferably excitable by ionizing radiation. Sonosensitizing compounds in the combination that are not excitable by ionizing radiation can be excited by energy transfer from activated sonosensitizing compounds.

Sonosensitizing compounds can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known neuroprotective agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from 0.0001 or 0.001 or 0.01 or 0.1 or 1 or 10 or 100 mg/kg of compound to 0.0005 or 0.005 or 0.05 or 0.5 or 5 or 50 or 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the sonosensitizing compound can be formulated into a liquid composition, a solid composition, or an aerosol composition. The liquid composition can include, by way of illustration, one or more sonosensitizing compounds dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Sonosensitizing compounds described herein can be administered parenterally or intraperitoneally. Solutions or suspensions of these compounds or a pharmaceutically acceptable salts, hydrates, or esters thereof can be prepared in water suitably mixed with a surfactant such as hydroxylpropylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Sonosensitizing compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a sonosensitizing compound and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Sonosensitizing compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce sonosensitizing compound into host cells either in vitro or in vivo. Lipid formulations and nanocapsules can be prepared by methods known in the art.

To increase the effectiveness of the sonosensitizing compounds, it can be desirable to combine a compound with other agents effective in the treatment of the target disease or condition. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

The invention is useful for the treatment and diagnosis of disease states, particularly for the destruction of infectious organisms, hyperproliferating cells, and tumor cells. Preferred sonosensitizing compounds: (i) are metal-based coordination complexes; (ii) absorb and are activated by ultrasound; (iii) kill human cancer cells in culture and in animals, and (iv) destroy bacteria and antibiotic-resistant bacteria.

The invention will be illustrated in more detail with reference to the following Examples, but it should be understood that the present invention is not deemed to be limited thereto.

EXAMPLES

Example 1

It is well established that SDT is performed by exposing the cell or tissue of interest to US at varying frequency and power density. Ruthenium or Osmium sonosensitizers (diluted in water or propylene glycol at 2 mM stock concentration) are utilized in various treatment modalities combined with sonodynamic therapy to test for synergistic effects.

In in vitro cultures, SDT was performed using US at 20% duty cycle at a frequency of 1 MHz and a power from 0.5 to 2 W/cm$^2$ on TLD-1433, which has the structure shown below.

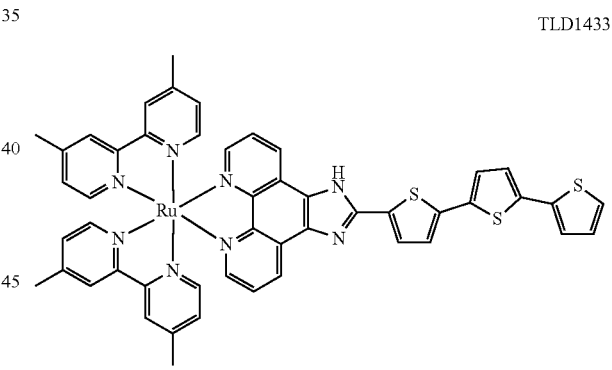

TLD1433

A control sample was measured in parallel. As shown in FIG. 1A, TLD-1433 showed pure SDT effect of about 47% in AY27 cells (at 2 W/cm$^2$) and about 33% in RG2 cells (at 0.5 W/cm$^2$), wherein cell kill was calculated by subtraction of TLD-1433 alone and US alone cell kills from the total SDT cell kill. The control sample (TLD-1433 alone) and US alone sample measured no more than 10% cell kill for both AY27 and RG2 cells.

In non-adherent GSC-818 cells (brain cancer stem-like), at 2 W/cm$^2$, about 45% cell kill was achieved upon subtraction of TLD-1433 alone (negligible) and US alone (about 26%) cell kills from the total SDT cell kill.

Figure 1B:
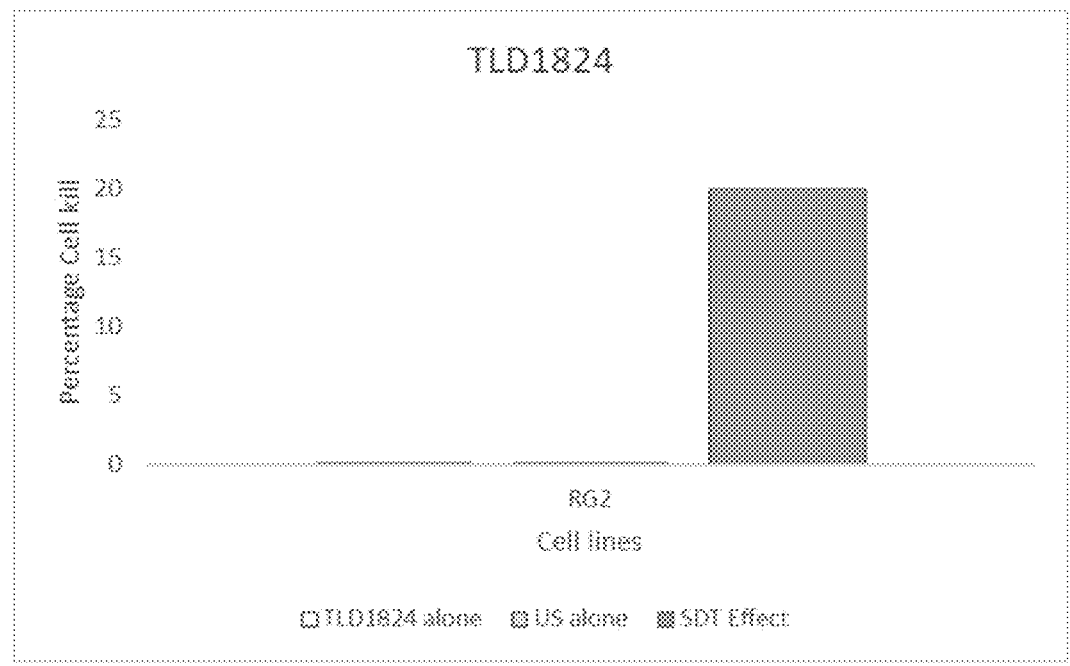
FIG. 1B is a bar graph of the percentage of RG2 cells killed in vitro after exposure to the combination of the sonosensitizing agent TLD-1824 and ultrasound.

As shown in FIG. 1B, SDT with TLD-1824 in RG2 cells caused about 20% cell kill as a pure SDT effect, with no dark toxicity and no US alone toxicity. TLD-1824 has the following structure.

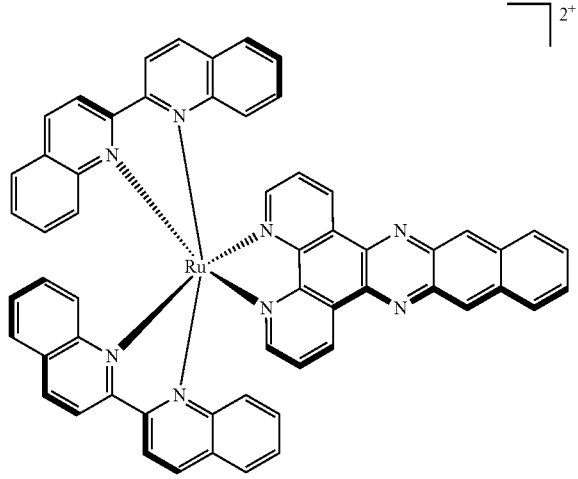

TLD1824

Example 2

Figure 2:
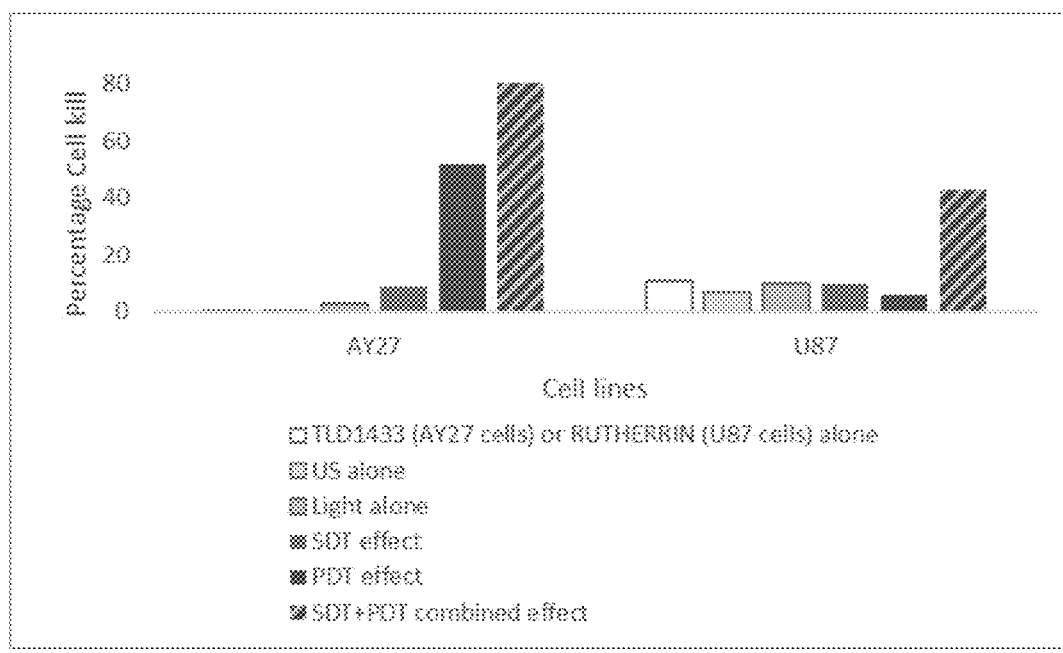
FIG. 2 is a bar graph of the percentage of AY27 and U87 cells killed in vitro after exposure to: (a) TLD1433 or RUTHERRIN; (b) ultrasound (US); (c) light; (d) TLD-1433 or RUTHERRIN +US ("SDT effect"); (e) TLD-1433 or RUTHERRIN +light ("PDT effect"); or (f) TLD-1433 or RUTHERRIN +US +light ("SDT +PDT combined effect").

As shown in FIG. 2, performing suboptimal SDT and photodynamic therapy ("PDT") together resulted in a synergistic effect, with high cell kill percentages as a result of the combined treatment. In AY27 (rat urothelial carcinoma) cells, a combined US (1 MHz, 0.5 W/cm², 20% duty cycle, 4 min of exposure) and visible light (635 nm, 20 J cm-2) mediated cell kill was achieved with Ru-based TLD-1433: about 84% pure effect for the combined treatment at negligible or very low (no more than about 3%) toxicity of TLD-1433 alone, US alone and light alone, about 9% pure effect of SDT, and about 52% of pure effect of PDT (light alone toxicity subtracted).

In U87 cells (human glioblastoma), combined SDT (1 MHz, 2 W/cm², 20% duty cycle, 1 min. of exposure) and PDT (635 nm, 40 J/cm²) also demonstrated a synergistic effect. The pure cell kill effect due to the combined treatment (about 43%), upon subtraction of US alone, light alone, and RUTHERRIN alone (about 29% together) cell kills from the total kill, was greater than the sum of the pure effects of the two separate treatments: SDT (about 10%) upon subtraction of the US alone (about 7%) cell kill and PDT (about 6%) upon subtraction of light alone (about 10%) cell kill; RUTHERRIN alone (about 11%) cell kill was also subtracted from the total kill at each of the separate treatments. The total cell kill in the combined treatment eventually reached about 83% as compared to the total kills at the two separate treatments (about 28% for SDT and about 27% for PDT).

Example 3

Figure 3:
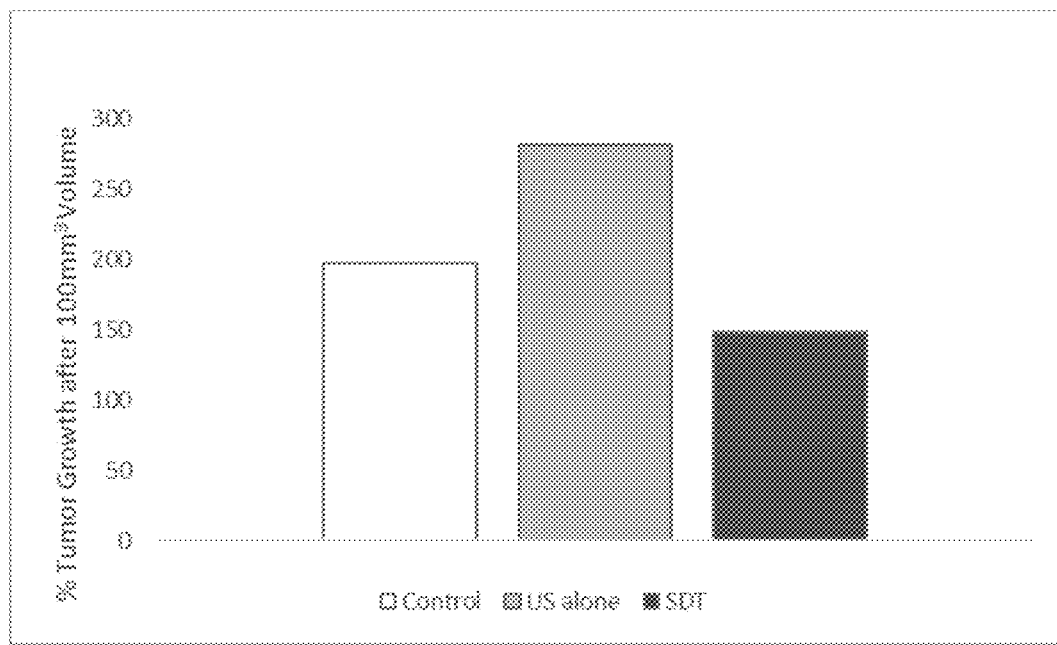
FIG. 3 is as bar graph of the percentage of tumor growth of 100 $mm^3$ tumors exposed to: (a) US; (b) US +RUTHERRIN; or (c) neither.

Metronomic SDT was performed in vivo on mice harboring hind-leg CT26.WT subcutaneous tumors using non-thermal unfocused US at 1 MHz, 1 W/cm², and 30% duty cycle, with daily US exposures. RUTHERRIN injections were performed at 10 mg/kg i.v. every second day. FIG. 3 shows that SDT caused tumor growth delay up to 3 days from an initial tumor volume of 100 mm³. By day 3 post-SDT, the tumor volume growth was about 25% less than in the control group (no treatment) and about 47% less than in the US alone group. The use of MRI-guided focused continuous US is expected to further improve the efficacy of SDT in vivo.

Example 4

Figure 4A:
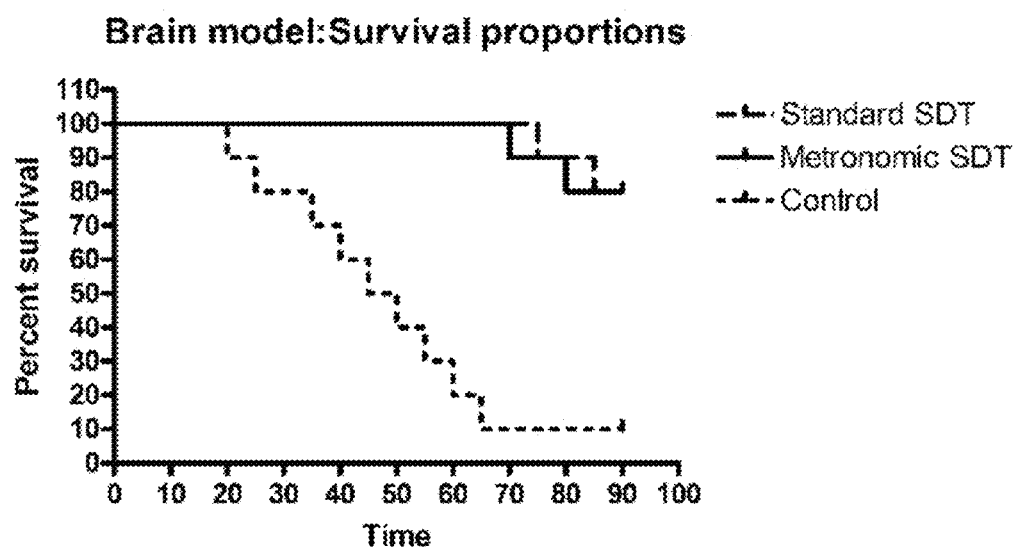
FIG. 4A is a graph showing the predicted survival rates of rats with brain tumors in response to in vivo SDT.
Figure 4B:
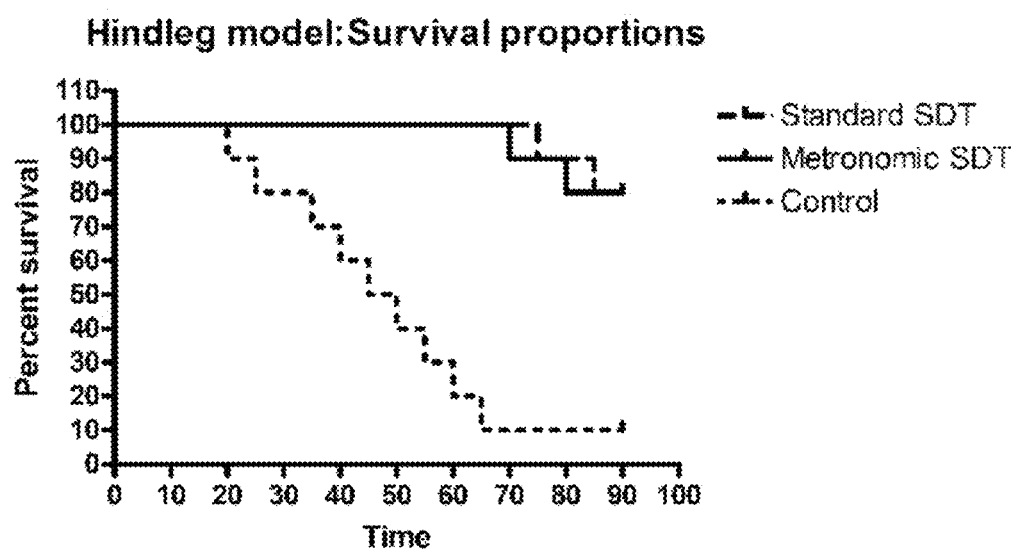
FIG. 4B is a graph showing the predicted survival rates of mice with hind-leg tumors in response to in vivo SDT.

Metronomic SDT using focused US is expected to be as effective as the standard SDT in brain or hind leg in vivo models, as shown in this prophetic example. Mice with hind-leg tumors (CT26.WT subcutaneous) and rats with brain tumors (RG2 orthotopic) are separated into three groups—a control group that did not receive treatment, a group receiving standard SDT using focused MRI guided US at 100% duty cycle and a power density of 5 W/cm², and a group receiving metronomic SDT at a duty cycle between 5% and 95% at 10 k W/cm² and a power density of 2 W/cm². FIGS. 4A and 4B show prophetically a decline in control group survival on day 20 and both mice and rat survival rates are 10% by day 65. Groups receiving standard SDT are expected to experience a decrease in survival rate for the first time on day 75, with 80% of both mice and rats remaining alive by day 85. Groups receiving metronomic SDT are expected to experience a decrease in survival rate for the first time on day 70, with 80% of both mice and rats alive by day 80.

In addition to the strong therapeutic advantages shown above, the addition of US could enable uniform distribution of sensitizing agents across the target tissue (e.g., a tumor), and lead to more homogeneous distribution thereof. This homogeneous drug distribution is one of the expected benefits of sonodynamic therapy using ultrasound, primarily for treatment of cancer in stroma-rich organs, such as pancreas, ovaries, stomach or prostate and/or in treatment of desmoplastic tumors.

While the invention has been described in detail and with reference to specific examples thereof, it will be apparent to one skilled in the art that various changes and modifications can be made therein without departing from the spirit and scope thereof.

What is claimed is:

1. A method for damaging a target material in an organism, said method comprising:
   administering to the organism a composition comprising a sonosensitizing compound having the formula (I):

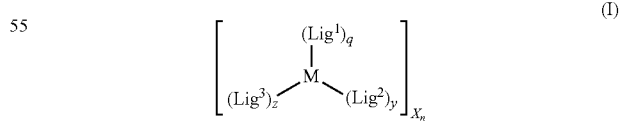

including hydrates, solvates, pharmaceutically acceptable salts, prodrugs and complexes thereof, wherein:

M is osmium or ruthenium;

X is selected from the group consisting of Cl⁻, PF$_6^-$, Br⁻, BF$_4^-$, ClO$_4^-$, CF$_3$SO$_3^-$, and SO$_4^{-2}$;

n=0, 1, 2, 3, 4, or 5;

q is independently at each occurrence 0, 1, or 2;
y is independently at each occurrence 0, 1, or 2;
z is independently at each occurrence 1, 2, or 3;
q+y+z=3;
Lig$^1$ is a bidentate ligand that at each occurrence is each independently selected from the group consisting of

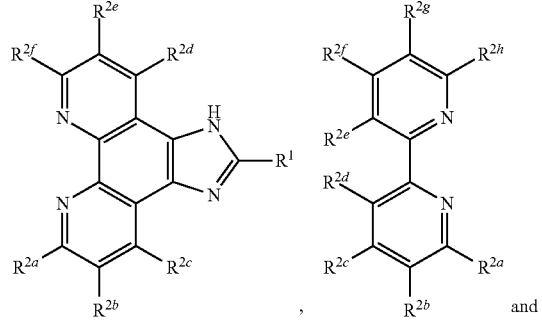

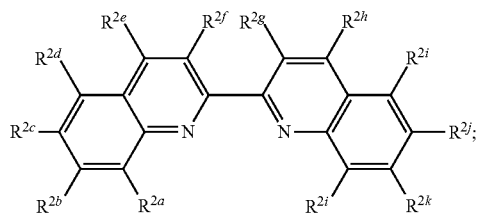

Lig$^2$ is a bidentate ligand that at each occurrence is each independently selected from the group consisting of

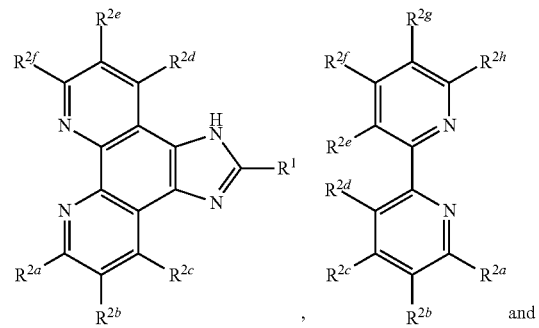

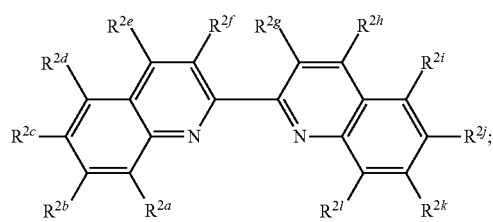

Lig$^3$ is a bidentate ligand that is

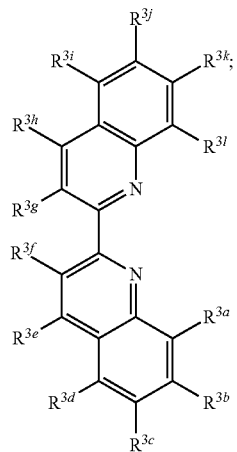

R$^1$ is selected from the group consisting of

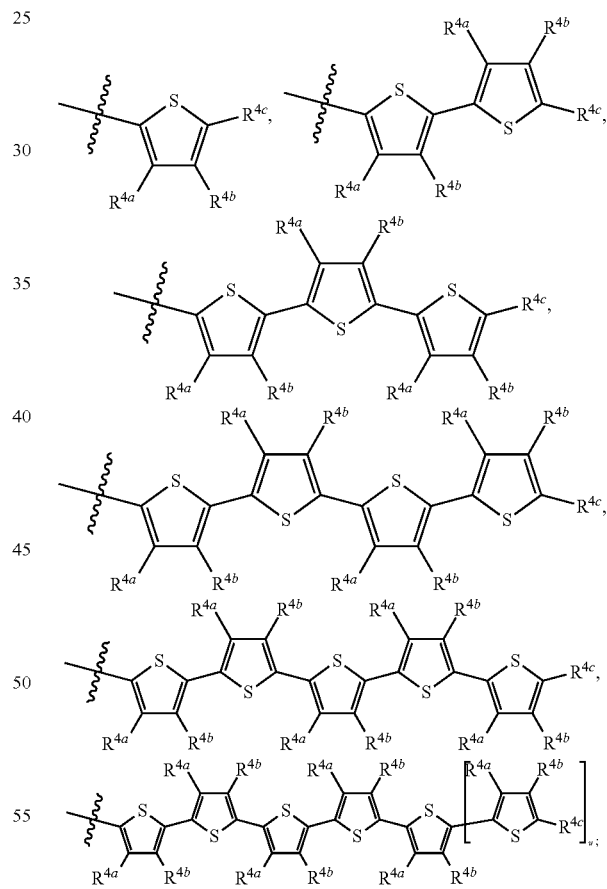

u is an integer from 1 to 10;
R$^{2a}$, R$^{2b}$, R$^{2c}$, R$^{2d}$, R$^{2e}$, R$^{2f}$, R$^{2g}$, R$^{2h}$, R$^{2i}$, R$^{2j}$, R$^{2k}$, and R$^{2l}$ at each occurrence are each independently selected from the group consisting of hydrogen, C$_{1-6}$ optionally substituted alkyl, C$_{1-6}$ optionally substituted branched alkyl, C$_{3-7}$ optionally substituted cycloalkyl, C$_{1-6}$ optionally substituted haloalkyl, C$_{1-6}$ optionally substituted alkoxy, CO$_2$R$^5$, CONR$^6_2$, NR$^7_2$, SO$_3$H, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$, $R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl; and $R^8$ at each occurrence are each independently selected from the group consisting of hydrogen and optionally substituted alkyl; and exposing the sonosensitizing compound to an activating energy, wherein the target material comprises at least one of cells and microorganisms, and the activating energy comprises ultrasound effective to trigger the sonosensitizing compound to damage the target material.

2. The method of claim 1, wherein the target material comprises hyperproliferating cells in the organism, and the method is effective to inhibit proliferation of the hyperproliferating cells in the organism or to destroy the hyperproliferating cells in the organism.

3. The method of claim 1, wherein the target material comprises microorganisms selected from the group consisting of bacteria, viruses, and fungi, and the method is effective to destroy the microorganisms.

4. The method of claim 1, wherein the organism is a human.

5. The method of claim 1, wherein the composition is administered by topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, rectal or extracorporeal routes.

6. The method of claim 1, wherein the composition is pharmaceutically acceptable and further comprises at least one pharmaceutically acceptable carrier, excipient, or diluent.

7. The method of claim 1, wherein the composition further comprises a metal-binding glycoprotein, a glycated or non-glycated form thereof.

8. The method of claim 7, wherein the metal-binding glycoprotein is transferrin.

9. The method of claim 1, wherein the ultrasound is administered in a continuous fashion at 100% duty cycle.

10. The method of claim 9, wherein the ultrasound is administered at a power of 0.01 W/cm² to 10 W/cm².

11. The method of claim 1, wherein the ultrasound is administered in a pulsed fashion at a duty cycle between 5% and 95%.

12. The method of claim 11, wherein the ultrasound is administered at a power of 10 W/cm² and frequency between 10 Hz to 10 MHz.

13. The method of claim 1, wherein the sonosensitizing compound is administered in combination with electromagnetic radiation.

14. The method of claim 13, wherein the combination of the sonosensitizing compound and the electromagnetic radiation is synergistically effective.

15. The method of claim 14, wherein the electromagnetic radiation comprises infrared or visible light.

16. The method of claim 15, wherein light is emitted from a laser.

17. The method of claim 14, wherein the electromagnetic radiation comprises ionizing radiation.

18. A method for damaging a target material in an organism, said method comprising:

administering to the organism a composition comprising a sonosensitizing compound having a structure selected from the group consisting of:

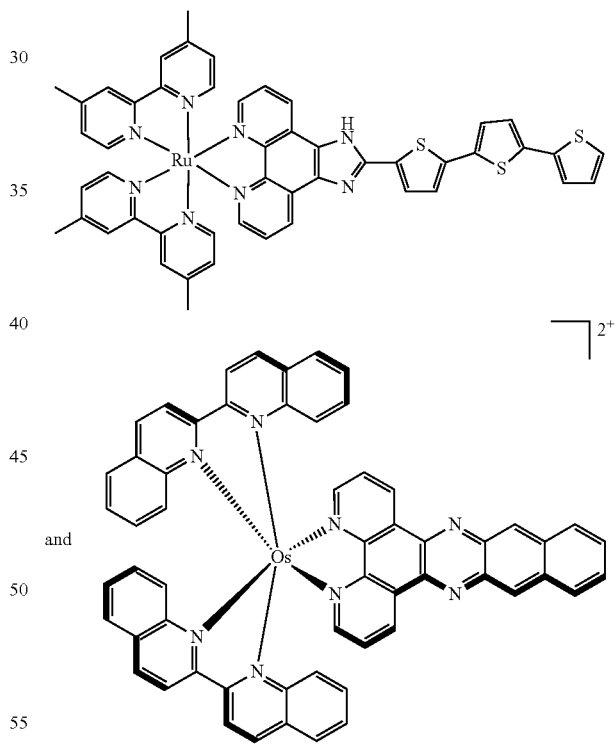

and including hydrates, solvates, pharmaceutically acceptable salts, prodrugs and complexes thereof, and exposing the sonosensitizing compound to an activating energy, wherein the target material comprises at least one of cells and microorganisms, and the activating energy comprises ultrasound effective to trigger the sonosensitizing compound to damage the target material.

19. The method of claim 18, wherein the ultrasound is administered: (a) in a continuous fashion at 100% duty cycle at a power of 0.01 W/cm² to 10 W/cm²; or (b) in a pulsed fashion at a duty cycle between 5% and 95% at a power of 10 W/cm² and a frequency between 10 Hz to 10 MHz.

20. The method of claim 19, wherein the composition further comprises transferrin and at least one pharmaceutically acceptable carrier, excipient, or diluent.

21. The method of claim 20, wherein the sonosensitizing compound has the following structure:

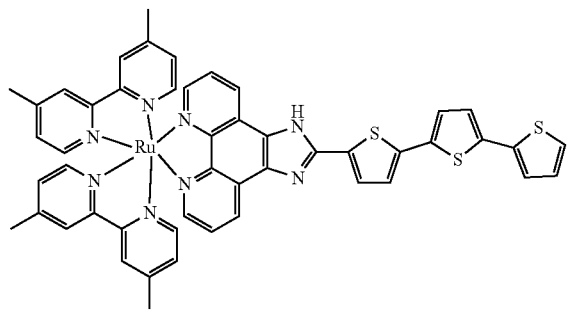

or is a hydrate, solvate, pharmaceutically acceptable salt, prodrug or complex thereof.

22. The method of claim 20, wherein the sonosensitizing compound has the following structure:

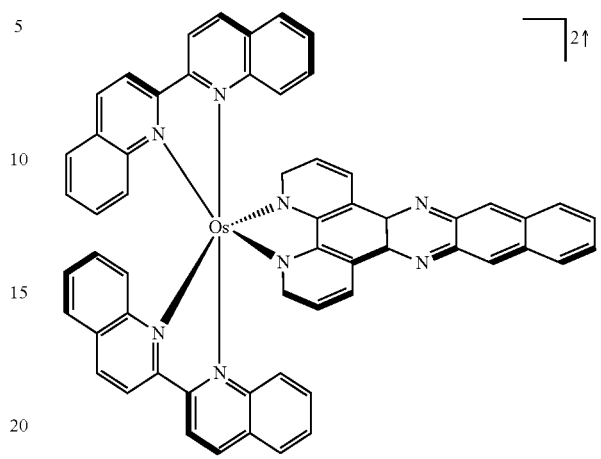

or is a hydrate, solvate, pharmaceutically acceptable salt, prodrug or complex thereof.

* * * * *